(12) United States Patent
Howard et al.

(10) Patent No.: US 11,452,613 B2
(45) Date of Patent: Sep. 27, 2022

(54) VERTEBRAL IMPLANTS AND METHODS FOR INSTALLATION THEREOF

(71) Applicant: GLOBUS MEDICAL, INC., Audubon, PA (US)

(72) Inventors: George Howard, Green Lane, PA (US); James Himmelberger, Souderton, PA (US); Jason Gray, East Greenville, PA (US); Colm McLaughlin, Glenside, PA (US); Noah Hansell, King of Prussia, PA (US); Mark Weiman, Downingtown, PA (US)

(73) Assignee: Globus Medical, Inc., Audubon, PA (US)

( * ) Notice: Subject to any disclaimer, the term of this patent is extended or adjusted under 35 U.S.C. 154(b) by 159 days.

(21) Appl. No.: 16/507,494

(22) Filed: Jul. 10, 2019

(65) Prior Publication Data
US 2020/0000604 A1  Jan. 2, 2020

Related U.S. Application Data

(63) Continuation of application No. 14/881,507, filed on Oct. 13, 2015, now Pat. No. 10,376,373, which is a continuation-in-part of application No. 14/580,273, filed on Dec. 23, 2014, now Pat. No. 9,801,730.

(51) Int. Cl.
*A61F 2/44*   (2006.01)
*A61F 2/46*   (2006.01)
*A61F 2/30*   (2006.01)
*A61B 17/80*  (2006.01)

(52) U.S. Cl.
CPC .............. *A61F 2/4465* (2013.01); *A61F 2/44* (2013.01); *A61F 2/442* (2013.01); *A61F 2/4425* (2013.01); *A61F 2/4455* (2013.01); *A61F 2/4611* (2013.01); *A61F 2/4684* (2013.01); *A61B 17/8095* (2013.01); *A61F 2002/3008* (2013.01); *A61F 2002/30228* (2013.01); *A61F 2002/30235* (2013.01); *A61F 2002/30383* (2013.01); *A61F 2002/30405* (2013.01); *A61F 2002/30433* (2013.01); *A61F 2002/30467* (2013.01); *A61F 2002/30495* (2013.01); *A61F 2002/30515* (2013.01); *A61F 2002/30517* (2013.01); *A61F 2002/30523* (2013.01); *A61F 2002/30538* (2013.01); *A61F 2002/30556* (2013.01); *A61F 2002/30565* (2013.01); *A61F 2002/443* (2013.01); *A61F 2002/4415* (2013.01); *A61F 2220/0041* (2013.01)

(58) Field of Classification Search
CPC ....... A61F 2/4455; A61F 2/4465; A61F 2/447
See application file for complete search history.

(56) References Cited

U.S. PATENT DOCUMENTS

| | | |
|---|---|---|
| 8,202,321 B2 | 6/2012 | Gerner |
| 8,282,683 B2 | 10/2012 | McLaughlin et al. |
| 2002/0138146 A1 | 9/2002 | Jackson |
| 2003/0176925 A1* | 9/2003 | Paponneau ........... A61F 2/4465 623/17.16 |

(Continued)

*Primary Examiner* — Julianna N Harvey

(57) ABSTRACT

Embodiments herein are generally directed to vertebral implants and implant trials for use with vertebral implant assemblies. In some embodiments, these implants and implant trials may be used in conjunction with corpectomy procedures.

15 Claims, 16 Drawing Sheets

(56) References Cited

U.S. PATENT DOCUMENTS

| | | | |
|---|---|---|---|
| 2006/0241770 A1* | 10/2006 | Rhoda | A61F 2/442 623/17.15 |
| 2006/0293755 A1* | 12/2006 | Lindner | A61F 2/442 623/17.15 |
| 2007/0191954 A1* | 8/2007 | Hansell | A61F 2/4611 623/17.15 |
| 2008/0281424 A1 | 11/2008 | Parry et al. | |
| 2010/0324687 A1* | 12/2010 | Melkent | A61F 2/44 623/17.16 |
| 2011/0251691 A1* | 10/2011 | McLaughlin | A61F 2/44 623/17.16 |
| 2012/0209384 A1* | 8/2012 | Arnold | A61F 2/4465 623/17.15 |
| 2012/0232660 A1* | 9/2012 | Davenport | A61F 2/4455 623/17.16 |
| 2013/0253650 A1 | 9/2013 | Ashley et al. | |
| 2013/0310938 A1* | 11/2013 | Sournac | A61F 2/44 623/17.15 |
| 2014/0172103 A1 | 6/2014 | O'Neil et al. | |
| 2014/0207236 A1* | 7/2014 | Prevost | A61F 2/4425 623/17.16 |
| 2016/0100955 A1* | 4/2016 | Stinchfield | A61F 2/44 623/17.15 |

* cited by examiner

VERTEBRAL IMPLANTS AND METHODS FOR INSTALLATION THEREOF

CROSS-REFERENCE TO RELATED REFERENCES

The present application is a continuation of U.S. patent application Ser. No. 14/881,507 filed on Oct. 13, 2015 which is a continuation-in-part application that claims priority to U.S. Ser. No. 14/580,273, filed Dec. 23, 2014, which is hereby incorporated by reference in its entirety.

FIELD OF THE INVENTION

The present invention relates to vertebral implants, implant trials, and methods used to install these devices.

BACKGROUND OF THE INVENTION

Many types of spinal irregularities can cause pain, limit range of motion, or injure the nervous system within the spinal column. These irregularities can result from, without limitation, trauma, tumor, disc degeneration, and disease. One example of a spinal irregularity is spinal stenosis, the narrowing of a spinal canal, which can result in the compression of spinal nerves such as the spinal cord or cauda equina. In turn, the nerve compression can result in pain, numbness, or weakness. Spinal stenosis may be caused by one or more conditions such as development of bone spurs, thickening of ligaments, fractures, and disc degeneration (e.g., due to arthritis).

Treatment of spinal stenosis can include, for example, a surgical procedure to expand the spinal canal by modifying or removing at least a part of a vertebra, as in a laminoplasty, laminectomy, or corpectomy. In a corpectomy, the vertebral bodies of one or more vertebrae adjacent to the compressed nerve can be removed, thereby expanding the spinal canal. Subsequently, a cage or other prosthetic may be inserted into the resulting cavity and may be used to subsequently stabilize the spine, either alone or in combination with one or more additional devices such as rods, screws, and/or plates.

SUMMARY OF THE INVENTION

Some embodiments herein are directed to a polyaxial endplate assembly that can include a locking member comprising a neck portion extending from a rounded head portion, the neck portion comprising a tapered slot extending therethrough; an articulable plate member comprising a plate portion extending from a rounded compressible body portion, the rounded compressible body portion defining a cavity configured to receive the rounded head portion of the locking member therein and an aperture configured to receive the neck portion of the locking member therethrough; a receiving member comprising an axial conduit comprising a constant diameter section and a variable diameter section, first and second tapered holes defining a tapered channel which intersects the conduit, and a receptacle which intersects the tapered channel, wherein the variable diameter section is configured to receive the rounded compressible body portion of the articulable plate member therein; a wedge member comprising a tapered transverse cross section and configured to be received within the channel of the receiving member; and a securing element configured to be received within the receptacle of the receiving member.

Other embodiments herein are directed to a polyaxial endplate assembly that can include a locking member comprising a neck portion extending from a rounded head portion, the neck portion comprising a tapered slot extending therethrough; an articulable plate member comprising a plate portion extending from a rounded body portion, the rounded body portion comprising a plurality of tabs defining a concave cavity and a central aperture; a receiving member comprising an axial conduit comprising a constant diameter section and a variable diameter section, a tapered channel which intersects the axial conduit, and a receptacle which intersects the tapered channel; a wedge member comprising a tapered transverse cross section; and a securing element configured to stabilize an orientation of the plate member relative to the receiving member.

Yet other embodiments herein are directed to a polyaxial endplate assembly that can include a locking member comprising a neck portion extending from a rounded head portion, the neck portion comprising a tapered slot extending therethrough; an articulable plate member comprising a plate portion extending from a rounded body portion, the rounded body portion comprising a plurality of tabs defining a concave cavity and a central aperture; a receiving member comprising an axial conduit comprising a constant diameter section and a variable diameter section, first and second tapered holes defining a tapered channel which intersects the conduit, and a receptacle which intersects the tapered channel; a wedge member configured to apply a force to the receiving member and the locking member; and a securing element configured to apply a force to the wedge member.

Some embodiments herein are directed to a method of installing a vertebral implant assembly that can include providing a vertebral implant assembly that can include a vertebral implant comprising a first engagement member; and a first polyaxial endplate assembly comprising a first receiving member having a tapered channel, a first articulable plate member articulably disposed within the receiving member, a first locking member disposed within the articulable plate member, and a first wedge member slideably disposed within the tapered channel; coupling the first polyaxial endplate assembly with the first engagement member; and applying force to the first wedge member to stabilize an orientation of the articulable plate member of the first polyaxial assembly relative to the vertebral implant.

Other embodiments herein are directed to a method of installing a vertebral implant assembly that can include providing a vertebral implant comprising a first polyaxial endplate assembly and a second polyaxial endplate assembly, wherein the first polyaxial endplate assembly comprises a first articulable plate member and a first wedge member and the second polyaxial endplate assembly comprises a second articulable plate member and a second wedge member; applying force to the first wedge member to stabilize an orientation of the first articulable plate member relative to the vertebral implant; and applying force to the second wedge member to stabilize an orientation of the second articulable plate member relative to the vertebral implant.

Yet other embodiments herein are directed to a method of installing a vertebral implant assembly that can include providing an expandable vertebral implant comprising a first engagement member and a second engagement member; coupling a first polyaxial endplate assembly with the first engagement member, wherein the first polyaxial endplate assembly comprises a first receiving member, a first articulable plate member, and a first wedge member; coupling an second polyaxial endplate assembly with the second engagement member, wherein the second polyaxial endplate assembly comprises a second articulable plate member and a second wedge member; expanding the vertebral implant from a first height to a second height; applying force to the first wedge member to stabilize an orientation of the first articulable plate member of the first polyaxial endplate assembly relative to the vertebral implant; and applying force to the second wedge member to stabilize an orientation of the second articulable plate member of the second polyaxial endplate assembly relative to the vertebral implant.

Some embodiments herein are directed to a polyaxial endplate assembly that can include an articulable plate member comprising a plate portion extending from a rounded compressible body portion, the body portion defining a cavity therein; a clamp assembly comprising first and second clamp members each comprising a central receptacle and an interior surface configured to engage the plate member, and a securing element configured to be received within the receptacles of the first and second clamp members; and a receiving member comprising a convex exterior surface configured to be received within the cavity of the body portion.

Other embodiments herein are directed to a polyaxial endplate assembly that can include an articulable plate member comprising a plate portion extending from a rounded body portion, the body portion comprising a plurality of tabs and defining a cavity therein; first and second clamp members each comprising a central receptacle and an interior surface configured to engage the plate member; a receiving member comprising a rounded portion configured to be received within the cavity of the body portion; and a securing element configured to stabilize an orientation of the plate member relative to the receiving member.

Yet other embodiments herein are directed to a polyaxial endplate assembly that can include an articulable plate member comprising a plate portion extending from a rounded body portion, the body portion comprising a plurality of tabs and defining a cavity therein; first and second clamp members each comprising an interior surface configured to engage the plate member and further comprising a central protrusion having a receptacle therein; a receiving member comprising a rounded portion configured to be received within the cavity of the body portion; and a securing element configured to be received within both receptacles of the first and second clamp members.

Some embodiments herein are directed to a method of installing a vertebral implant assembly that can include providing a vertebral implant assembly that can include a vertebral implant comprising a first engagement member; and a first polyaxial endplate assembly comprising a first receiving member, a first articulable plate member, and a first clamping assembly, wherein the first receiving member is at least partially disposed within a cavity of the first articulable plate member and the first clamp assembly is engaging a body portion of the first articulable plate member; coupling the first polyaxial endplate assembly with the vertebral implant; and applying a force to the first articulable plate member to stabilize an orientation of the first articulable plate member relative to the vertebral implant.

Still other embodiments herein are directed to an endplate trial that can include a coupling element configured to reversibly engage at least a portion of a vertebral implant device.

Further areas of applicability of the present invention will become apparent from the detailed description provided hereinafter. It should be understood that the detailed description and specific examples, while indicating certain embodiments of the invention, are intended for purposes of illustration only and are not intended to limit the scope of the invention.

BRIEF DESCRIPTION OF THE DRAWINGS

The present embodiments will become more fully understood from the detailed description and the accompanying drawings, wherein.

DETAILED DESCRIPTION

Figure 1A:
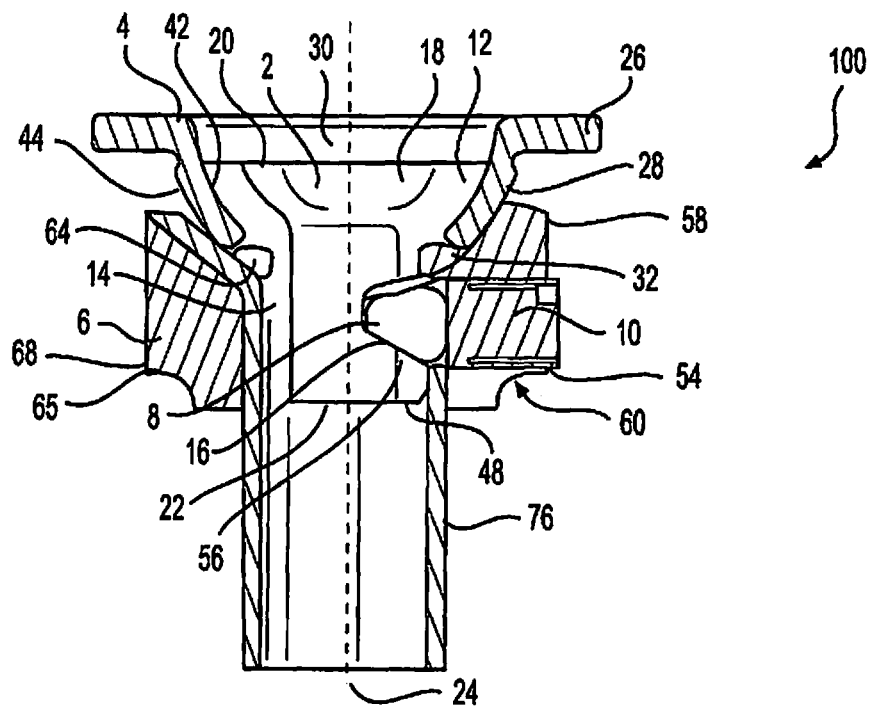
FIG. 1A illustrates a cross-sectional view of a polyaxial endplate assembly as described herein.

In a corpectomy procedure, a spinal canal can be expanded, and pressure on a compressed nerve can be relieved, by partially or completely removing one or more vertebral bodies adjacent to the compressed nerve. One or more intervertebral discs and other associated materials may also be removed. An implant (e.g., a cage, spacer, vertebral body replacement, or other prosthetic) may be inserted into the resulting cavity to subsequently stabilize the spine. In some instances, the implant can include an optionally-expandable body coupled to superior and inferior endplates that have been selected to match the contours of the vertebral cavity. Prior to insertion, a surgeon or other practitioner may approximate the appropriate size and lordotic or kyphotic angle of the endplates (e.g., via imaging and/or physical measurement devices such as a caliper or implant trial), select the endplates that most closely match the desired angles, and assemble the implant by connecting the selected endplates with the implant body. Once the implant is assembled and inserted into the vertebral cavity, the surgeon may be unable to make further in-situ adjustments to the angles of the endplates. A disparity between the angles of the endplates and the angles of the adjacent vertebral bodies can result in subsidence or sagittal imbalance. Accordingly, disclosed herein are new and improved modular vertebral implants and assemblies having polyaxial endplates, the angles of which can be pivotably adjusted after assembly and/or implantation.

Components of all of the devices disclosed herein can be made of materials known to those skilled in the art, including metals (e.g., titanium), metal alloys (e.g., stainless steel and cobalt-chromium), ceramics, polymers (e.g., poly ether ether ketone (PEEK), polyphenylene sulfone (PPSU), polysulfone (PSU), polycarbonate (PC), polyetherimide (PEI), polypropylene (PP), polyacetals, or mixtures or co-polymers thereof), allograft, and/or combinations thereof. In some embodiments, the devices may include radiolucent and/or radiopaque materials. The components can also be machined and/or manufactured using techniques known to those skilled in the art. For example, polymeric components may be injection-molded or blow-molded. Additionally, the devices disclosed herein may be used together with materials that encourage bone growth, such as bone graft material, demineralized bone matrix, bone chips, and/or bone morphogenetic proteins. In some embodiments, these materials may advantageously be packed into hollow areas of the devices described herein.

As used herein the terms "proximal" and "distal" are utilized generally with reference to an implant or other device with which the polyaxial endplate assemblies and endplate trial assemblies described herein may couple. For example, the end of an endplate assembly that is closer to the implant or other device, after the entire assembly has been put together, may be referred to as the "proximal" end, whereas the end of the endplate assembly that is farther from the implant or other device (e.g., the end that may be configured to engage a vertebral body) may be referred to as the "distal" end. Similarly, the terms "superior," "inferior," "top," and "bottom," and the like may be used herein for descriptive purposes and do not limit the orientation(s) in which the devices may be used. For example, those skilled in the art may appreciate that a "superior" endplate may be installed in an inferior position, and vice versa. Accordingly, a feature described as being on top may actually be oriented towards the bottom after installation.

In some embodiments, the present application describes a polyaxial endplate assembly that can be attached to or form part of an interbody spacer such as a corpectomy device. The polyaxial endplate assembly can comprise an endplate in the form of an articulatable plate member, a receiving member attachable to the corpectomy device for receiving the articulable plate member, and a locking member received within the articulatable plate member. The polyaxial endplate assembly can replace an endplate (such as reference numeral 20 in FIG. 2of U.S. 2011/0251691 to McLaughlin, herein incorporated by reference in its entirety). Advantageously, the articulatable plate member of the polyaxial endplate assembly is capable of pivoting and rotation, thereby accommodating different lordosis and kyphosis of a patient. The articultable plate member is capable of pivoting and rotating naturally relative to a patient's anatomy until it is secured in position via the locking member. These features are described below.

Turning now to FIGS. 1A-E, polyaxial endplate assembly 100 is illustrated in accordance with embodiments described herein. As illustrated in FIG. 1A, the polyaxial endplate assembly 100 can include a locking member 2, an articulable plate member 4, a receiving member 6, a wedge member 8, and a securing element 10.

The locking member 2 can include a rounded head portion 12 and a neck portion 14 extending therefrom. The rounded head portion 12 can have a convex outer surface. In some embodiments, the rounded head portion 12 can include an at least partially spherical, spheroidal, or ovoidal outer surface. The outer diameter of the rounded head portion 12 can vary axially (e.g., can decrease in a proximal direction). The neck portion 14 of the locking member 2 can include a cylindrical outer surface. As illustrated in FIG. 1A, the neck portion 14 can also include a tapered slot 16 extending therethrough. The tapered slot 16 can define a trough that extends transverse or perpendicular to the longitudinal axis 24 of the locking member 2. The tapered slot 16 can have a variable height. For example, the height of the tapered slot 16, as measured longitudinally, can decrease as a depth of the tapered slot 16, as measured transversely, increases.

As illustrated in FIG. 1A, the locking member 2 can be hollow (e.g., can include a conduit 18 extending along a longitudinal axis 24 from a distal end 20 to a proximal end 22). The conduit 18 can include a circular transverse cross section. In some embodiments, the diameter of the conduit 18 can vary along at least a portion of the longitudinal axis 24. In some embodiments, the conduit 18 can include a variable diameter section and a constant diameter section. As illustrated in FIG. 1A, the variable diameter section can be disposed within the rounded head portion 12 and the constant diameter section can be disposed within the neck portion 14. In these embodiments, the conduit 18 can define a cavity within the rounded head portion 12 having a rounded longitudinal cross section, as illustrated in FIG. 1A. In other embodiments, the cavity can have an angular (e.g., conical) longitudinal cross section. In the neck portion 14 of the locking member 2, the conduit 18 can define a hollow cylinder. Advantageously, the interaction between the locking member 2 and the wedge member 8 fixes the angular position of the articultable plate member, as discussed further below.

Figure 1B:
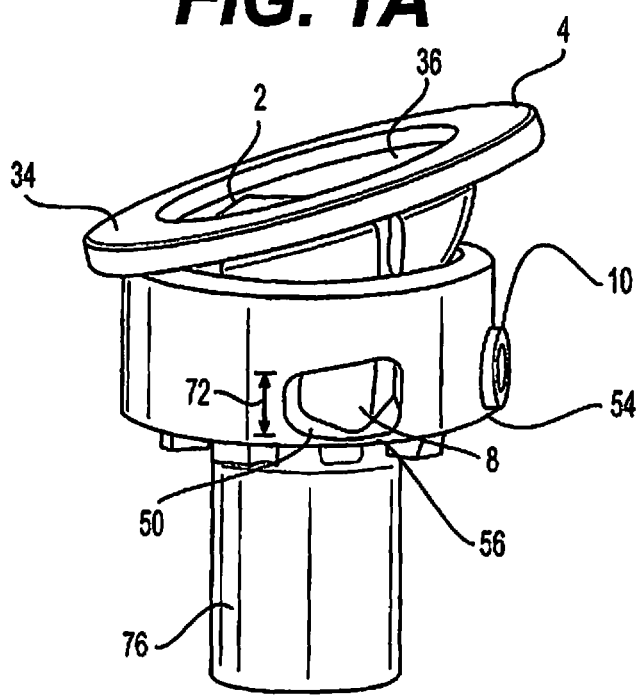
FIGS. 1B, 1C, and D illustrate perspective views of a polyaxial endplate assembly as described herein.

The articulable plate member 4 can include a plate portion 26 extending from a rounded body portion 28. The plate portion 26 can include a top or distal surface 34 and a central aperture 36, as illustrated in FIG. 1B. The distal surface 34 may be configured to engage or contact a vertebral body. Accordingly, the distal surface 34 may be contoured to correspond to the shape of a vertebral body. As illustrated, the distal surface 34 can be planar. However, in other embodiments, the distal surface 34 can be convex or concave. Additionally, the distal surface 34 may include one or more features to enhance the interaction or friction between the implant and the vertebral body or other bone feature. For example, the distal surface 34 can be roughened, and can include, for example, a plurality of teeth, bumps, peaks, grooves, and/or knurling. The distal surface 34 can include at least one engagement member. The engagement member can be configured to engage and/or apply force to a vertebral body. For example, the engagement member can be a spike. In some embodiments, the distal surface 34 can include a plurality of engagement members. The engagement member(s) can advantageously prevent sliding or other translational movement of the assembly after installation within the vertebral space. In other embodiments, the distal surface 34 can include an imaging member, such as one or more radiographic markers.

As illustrated in FIG. 1A, the rounded body portion 28 of the articulable plate member 4 can include a curved inner surface 42 and a curved outer surface 44. The curved inner surface 42 can define a concave cavity 30 therein and can include an aperture 32 therethrough. The central aperture 36 of the plate portion 26 may lead into the cavity 30. The cavity 30 can be configured to receive the rounded head portion 12 of the locking member 2. The curved inner surface 42 may be configured to contact the outer surface of the rounded head portion 12 of the locking member 2. The aperture 32 can be configured to receive the neck portion 14 of the locking member 2 therethrough, and may therefore have a diameter than is greater than an outer diameter of the neck portion 14. The aperture 32 may have a diameter that is less than a maximum diameter of the head portion 12 of the locking member 2, thereby preventing the locking member 2 from passing entirely through the articulable plate member 4.

Figure 1C:
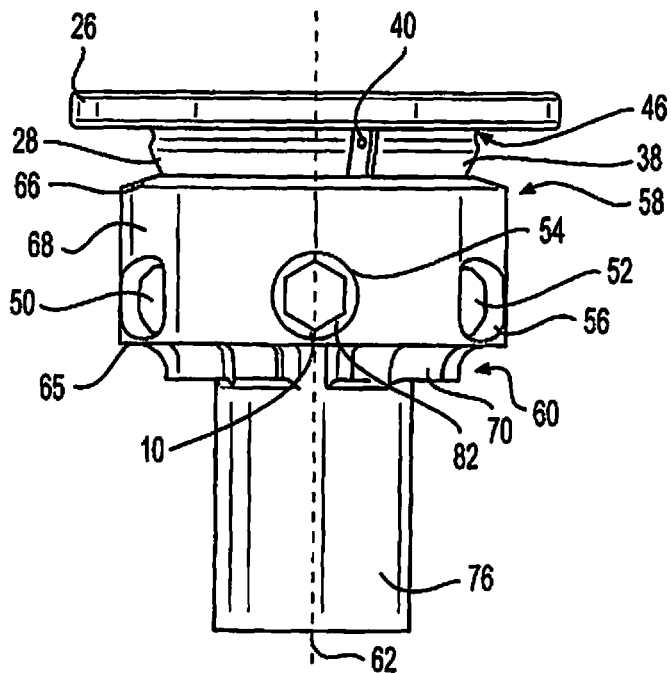
Figure 1D:
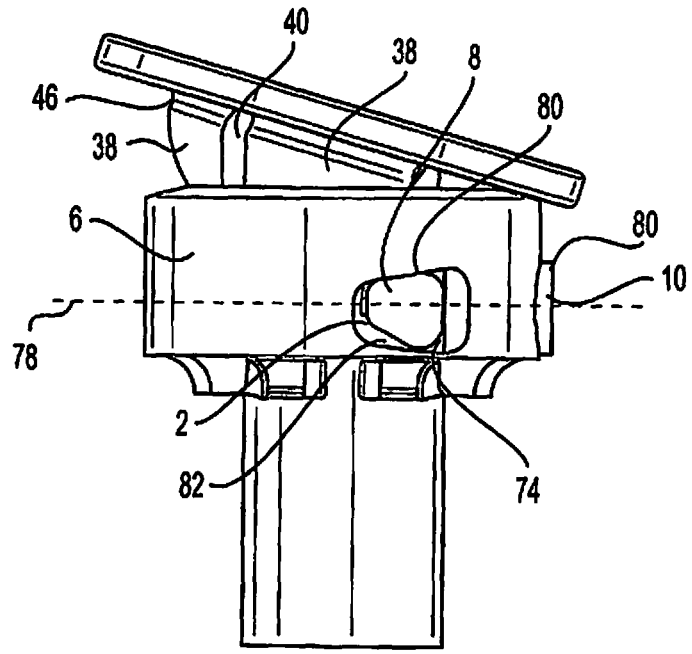
FIG. 1E illustrates a perspective view of a polyaxial endplate assembly engaged with a vertebral implant as described herein.

As illustrated in FIGS. 1C-D, the rounded body portion 28 can include a plurality of tabs 38. The tabs 38 can be separated by slots 40. The number of tabs 38 making up the rounded body portion 28 can vary, and can be, for example, in the range of from about two to about twelve. In some embodiments, the tabs 38 and slots 40 may be equally sized and spaced. In other embodiments, the tabs 38 and/or slots 40 may be of variable sizes. Advantageously, the rounded body portion 28 may be compressible, bendable, flexible, and/or constrictable (e.g., a force may be applied to the tabs 38 which causes the tabs 38 to flex inward, thereby reducing the volume of the cavity 30). Additionally, the outer surface 44 of the articulable plate member 4 may include a circumferential groove 46 or thinned section at an intersection between the body portion 28 and the plate portion 26. The circumferential groove 46 may advantageously enhance the movement of the tabs 38 and the overall flexibility of the rounded body portion 28, thereby enhancing engagement of the rounded body portion 28 with the locking member 2 and receiving member 6.

As illustrated in FIGS. 1A-C, the receiving member 6 can include a cylindrical side surface 68, a top surface 64 adjacent a distal end 58, and a bottom surface 65 adjacent a proximal end 60. The receiving member 6 can also include a chamfered edge 66 between the side surface 68 and the top surface 64. Additionally, the receiving member 6 can include an axial conduit 48, first and second tapered holes 50, 52 defining a tapered channel 56, and a receptacle 54 which intersects the tapered channel 56. The axial conduit 48 can extend along a longitudinal axis 62, illustrated in FIG. 1C, from distal end 58 to proximal end 60. The axial conduit 48 can include a circular transverse cross section. In some embodiments, the diameter of the axial conduit 48 can vary along at least a portion of the longitudinal axis 62. In some embodiments, the axial conduit 48 can include a variable diameter section and a constant diameter section. In some embodiments, the variable diameter section can define a concave socket (e.g., having a rounded or curved longitudinal cross section) bounded by top surface 64, as illustrated in FIG. 1A. In other embodiments, the socket can have an angular (e.g., conical) longitudinal cross section.

The first tapered hole 50 can be trapezoidal or rounded trapezoidal, as illustrated in FIGS. 1B-C. In some embodiments, the first tapered hole 50 can be asymmetrical along a horizontal plane (e.g., the first tapered hole 50 may be defined by an upper wall and a lower wall, wherein the lower wall is steeper than the upper wall, or vice versa). In other embodiments, it may be symmetrical. As illustrated in FIG. 1B, the first tapered hole 50 may have a height 72, wherein the height 72 decreases in a direction away from the receptacle 54. The second tapered hole 52 may have some or all of the same features as the first tapered hole 50, and may be symmetrical with respect to the first tapered hole 50. As described herein, the tapered channel 56 can extend in a straight line from the first tapered hole 50 to the second tapered hole 52. Additionally, the tapered channel 56 can intersect the axial conduit 48. As illustrated in FIG. 1A, the channel 56 of the receiving member 6 can be configured to at least partially overlap the tapered slot 16 of the locking member 2 when in an assembled configuration.

As illustrated in FIG. 1C, the receptacle 54 can include a longitudinal axis that is perpendicular to, and intersects, longitudinal axis 62 of the axial conduit 48. The longitudinal axis of the receptacle 54 can also be perpendicular to the tapered channel 56. In some embodiments, the receptacle 54 can include a cylindrical inner surface. The receptacle 54 can be configured to receive the securing element 10 therein. Accordingly, the receptacle 54 may include an engagement feature configured to engage and/or mate with the securing element 10. For example, the engagement feature can include threading or a cam groove. Advantageously, the orientation of the receptacle 54 can promote direct access to the receptacle 54, as compared to, for example, a receptacle that may involve side-to-side insertion of the securing element 10 (e.g., a receptacle that may be offset from and/or may not intersect with the axial conduit 48).

As illustrated in FIG. 1C, the receiving member 6 can include at least one coupling element 70, e.g., extending from the bottom surface 65 thereof. The coupling element 70 can be configured to engage a vertebral implant. In some embodiments, the coupling element can be a projection member, such as a tab, as illustrated in FIG. 1C. The projection member or tab can include a protrusion, such as a head or a hook that can be configured to be received within a groove or undercut in the vertebral implant. In other embodiments, the coupling element 70 can be a groove or slot configured to receive a portion of the vertebral implant therein. As illustrated in FIG. 1C, the receiving member 6 can include a plurality of coupling elements 70.

In some embodiments, the receiving member 6 may optionally include a neck portion 76 extending from proximal end 60, as illustrated in FIGS. 1A-C. The neck portion 76 can include a hollow cylinder (having, e.g., constant inner and outer diameters) in fluid communication and coaxial with the axial conduit 48. In these embodiments, the axial conduit 48 may be considered to pass through both the receiving member 6 and the neck portion 76. The receiving member 6 can have an outer diameter that is greater than an outer diameter of the neck portion 76. In some embodiments, the neck portion 76 may be configured to be received within an implant, such as the implants described in U.S. Publication No. 2011/0251691 entitled EXPANDABLE VERTEBRAL IMPLANT to McLaughlin, et al., hereby incorporated by reference herein in its entirety for all purposes.

As illustrated in FIGS. 1A-C, the wedge member 8 can include a tapered transverse cross section and can be configured to be received within the tapered channel 56 of the receiving member 6. The wedge member 8 can be an elongate and/or straight rod. As illustrated in FIG. 1A, the wedge member 8 can have a generally trapezoidal (e.g., rounded trapezoidal) cross section. For example, the transverse cross section of the wedge member 8 can have five sides connected by rounded or chamfered corners. The wedge member 8 can also have a rectangular longitudinal cross section. In some embodiments, the wedge member 8 may be asymmetrical along a longitudinal plane (e.g., horizontal plane 78, illustrated in FIG. 1D). For example, the wedge member 8 can include an upper wall 80 and a lower wall 82, wherein the lower wall 82 is steeper than the upper wall 80. In other embodiments, the upper wall 80 can be steeper than the lower wall 82. In some embodiments, the angle of the lower wall 82, relative to horizontal plane 78, can differ from the angle of the upper wall 80 by at least 10 degrees. In other embodiments, the angle of the lower wall 82, relative to horizontal plane 78, can differ from the angle of the upper wall 80 by at least 15 degrees. In yet other embodiments, the angle of the lower wall 82, relative to horizontal plane 78, can differ from the angle of the upper wall 80 by an amount in the range of from about 5 degrees to about 20 degrees. As illustrated in FIG. 1D, for example, the lower wall 82 may be configured to engage the locking member 2 and the upper wall 80 may be configured to engage the receiving member 6. Furthermore, the wedge member 8 may be configured to apply force to both the locking member 2 and the receiving member 6. Additionally, the wedge member 8 may be configured to fit (e.g., eccentrically or concentrically) within the tapered channel 56 of the receiving member 6 and the tapered slot 16 of the locking member 2.

The securing element 10 can include a first end 74 and a second end 80, wherein the first end 74 is configured to contact and/or apply force to the wedge member 8, as illustrated in FIG. 1D. The securing element 10 can also include a tool-receiving recess 82 at the second end 80, as illustrated in FIG. 1C. The securing element 10 can be configured to be received within the receptacle 54 of the receiving member 6, as illustrated in FIG. 1A. In some embodiments, the securing element 10 can be configured to be threaded into the receptacle 54, and can be, for example, a set screw. In other embodiments, the securing element 10 can be rotated into locking engagement with the receptacle 54, and can be, for example, a cam lock. As described herein, the securing element 10 can advantageously be configured to stabilize an orientation (e.g., an angle) of the articulable plate member 4 relative to the receiving member 6.

Some embodiments herein are directed to methods of installing a vertebral implant assembly that can include a vertebral implant and a first (e.g., superior or inferior) polyaxial endplate assembly, such as the polyaxial endplate assembly 100. These methods can include providing the first polyaxial endplate assembly 100 in an unassembled, partially assembled, or fully assembled state. In some embodiments where the first polyaxial endplate assembly 100 is partially or fully assembled, some or all of the components of the assembly 100 may be coupled or connected, but some or all of the components may still be capable of rotating, pivoting, and/or translating relative to one another.

Some embodiments can include providing the first polyaxial endplate assembly 100 in an assembled state. In these embodiments, the rounded head portion 12 of the first locking member 2 may be disposed or nested within the cavity 30 of the first articulable plate member 4, such that neck portion 14 has passed through the aperture 32. The body portion 28 of the first articulable plate member 4 may be disposed or nested within the variable diameter section of the first receiving member 6, and the neck portion 14 of the first locking member 2 may be disposed within the axial conduit 48 of the first receiving member 6. The tapered slot 16 of the first locking member 2 may be generally aligned with the tapered channel 56 of the first receiving member 6, and the first wedge member 8 may be slideably disposed therein. The first securing element 10 may be in loose engagement with the receptacle 54 (e.g., such that the first articulable plate member 4 is articulable or pivotable within the first receiving member 6), or may not be engaged with the receptacle 54. Those skilled in the art may appreciate that in the assembled state, the articulable plate member 4 may be able to articulate or pivot relative to the locking member 2 and/or the receiving member 6.

Figure 1E:
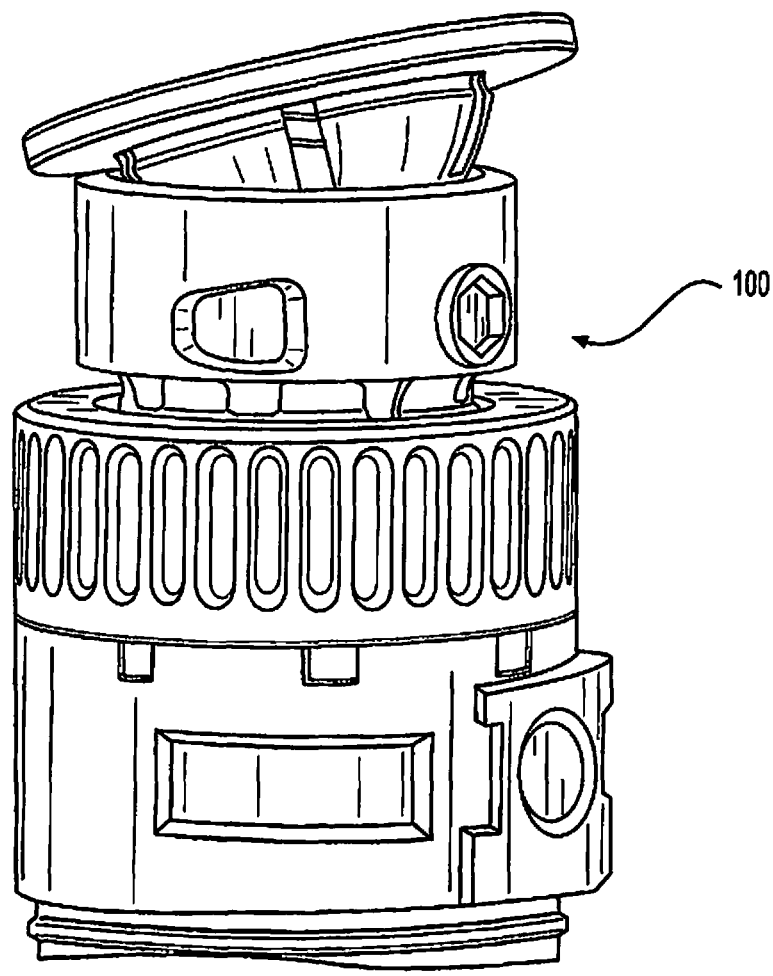

The method can also include providing a vertebral implant that can include a first (e.g., superior) engagement member and/or a second (e.g., inferior) engagement member. The vertebral implant can include, for example, a corpectomy implant, an interbody implant, a vertebral body replacement, a cage, or a spacer. In some embodiments, the vertebral implant can have a variable and/or adjustable height. In some embodiments the vertebral implant may be a vertically-expandable or extendable implant described in U.S. Publication No. 2011/0251691 to McLaughlin et al. Those skilled in the art may appreciate that the polyaxial endplate assemblies described herein may be used instead or in place of the endplates described in the aforementioned publication. One example of a vertebral implant is illustrated in FIG. 1E.

The superior engagement member of the vertebral implant can include a coupling element extending from a superior surface. The inferior engagement member can include a coupling element extending from an inferior surface. With regards to either the superior and/or inferior engagement members the coupling element may be, for example, a tab, notch and/or socket. In some embodiments, the superior and/or inferior engagement member(s) can include a plurality of tabs. In other embodiments, the superior and/or inferior engagement member(s) can include a plurality of notches.

The method can also include coupling a first (e.g., superior) polyaxial endplate assembly 100 with the first (e.g., superior) engagement member. In these embodiments, the receiving member 6 can include coupling element 70 (e.g., tab and/or notch) extending from proximal end 60. As described herein, the receiving member 6 can include a plurality of coupling elements 70. The step of coupling the first polyaxial endplate assembly with the first engagement member can include engaging the coupling element 70 of the receiving member 6 with the coupling element of the first engagement member. For example, this step can include interdigitating or dovetailing the coupling element 70 of the receiving member 6 (e.g., a tab or notch) with the coupling element of the first engagement member (e.g., a notch or tab).

In some embodiments, the receiving member 6 can additionally include a cylindrical neck portion 76. In these embodiments, the step of coupling the first polyaxial endplate assembly with the first engagement member can include inserting the cylindrical neck portion 76 into the socket of the vertebral implant, for example as illustrated in FIG. 1E.

The method can also include coupling a second (e.g., inferior) polyaxial endplate assembly with the second (e.g., inferior) engagement member. This step can be performed in substantially the same way as the coupling of the first polyaxial endplate assembly with the first engagement member. Those skilled in the art may appreciate that in some embodiments only one polyaxial endplate assembly may be used (e.g., inferior or superior), while in other embodiments two polyaxial endplate assemblies may be used (e.g., inferior and superior). Additionally, those skilled in the art may appreciate that steps described herein with respect to the first polyaxial endplate assembly can also be applied to installation of the second polyaxial endplate assembly.

Upon assembly, the method can also include inserting the vertebral implant assembly into a selected location, such as a cavity between two vertebral bodies created by a corpectomy or other procedure. In embodiments using an expandable vertebral implant, this step can additionally include expanding the vertebral implant from a first height to a second height, e.g., until the polyaxial endplate assembly contacts the vertebral body. Advantageously, those skilled in the art may appreciate that the articulable plate member of the vertebral implant assembly may be configured to pivot or articulate relative to the assembly, even after being put together. Accordingly, the angles of the polyaxial endplate assembly may be adjusted in situ to correspond to the topography of the adjacent vertebral body.

The method can also include applying force or pressure to the first wedge member 8. In some embodiments, the force can be applied to the first wedge member 8 through a first securing element 10. For example, in some embodiments the first securing element 10 can be a set screw. In these embodiments, the step of applying force to the first wedge member 8 can include threading the set screw into the receptacle 54 of the first receiving member 6 until the set screw contacts the first wedge member 8. Advantageously, those skilled in the art may appreciate that when coupled together, the position (e.g., angle) of the receptacle 54 of the first receiving member 6 may not be pivotable or articulable (e.g., may be fixed) relative to the overall vertebral implant assembly. Accordingly, this feature may enable the first securing element 10 to easily be guided to the receptacle 54, as the receptacle 54 may be generally held in place. As the set screw pushes the first wedge member 8 into the tapered slot 16 and the tapered channel 56, the lower wall 82 of the first wedge member 8 may apply a force (e.g., downward) to the first locking member 2 and the upper wall 80 may apply an opposite (e.g., upward) force to the first receiving member 6, thereby engaging, squeezing, and/or compressing the first articulable plate member 4 therebetween and locking, stabilizing, and/or securing the orientation (e.g., angle) of the first articulable plate member 4 relative to the vertebral implant assembly. For example, as shown in FIG. 1A, as the wedge member 8 is driven inward, this pushes downward on the first locking member 2 (abutting a bottom surface of the wedge member 8) and upward on the receiving member 6 (abutting a top surface of the wedge member 8), which thereby clamps the articulatable plate member 4 in a desired orientation. When in the locked, stabilized, and/or secured configuration, the first articulable plate member 4 may be effectively unable to pivot, articulate, and/or rotate relative to the first locking member 2 and/or the first receiving member 6.

Figure 2A:
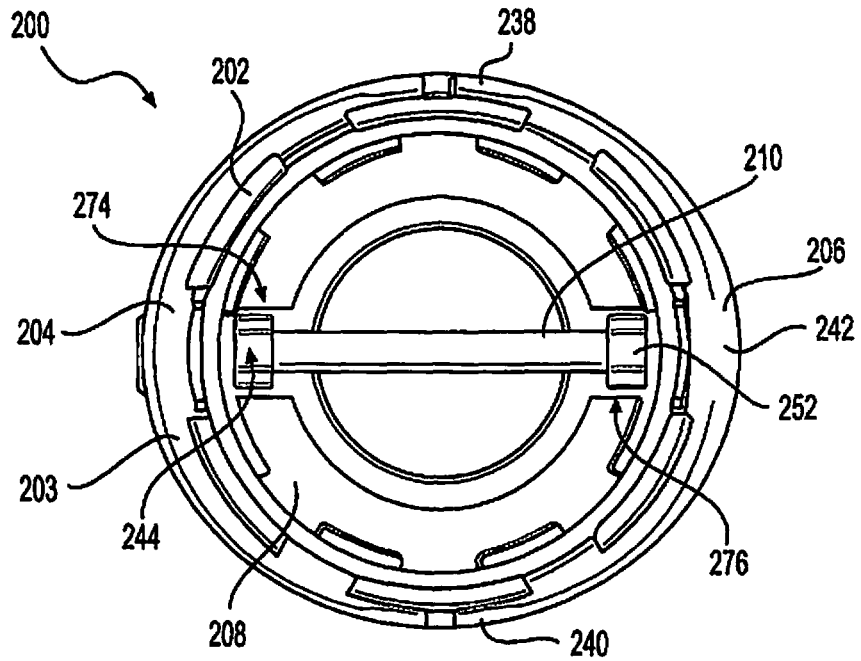
FIG. 2A illustrates a perspective bottom view of a polyaxial endplate assembly as described herein.

Turning now to FIGS. 2A-D, polyaxial endplate assembly 200 is illustrated in accordance with embodiments described herein. As illustrated in FIG. 2A, the polyaxial endplate assembly 200 can include an articulable plate member 202, a clamp assembly 203 comprising a first clamp member 204, second clamp member 206, and a securing element 210, and a receiving member 208.

Figure 2B:
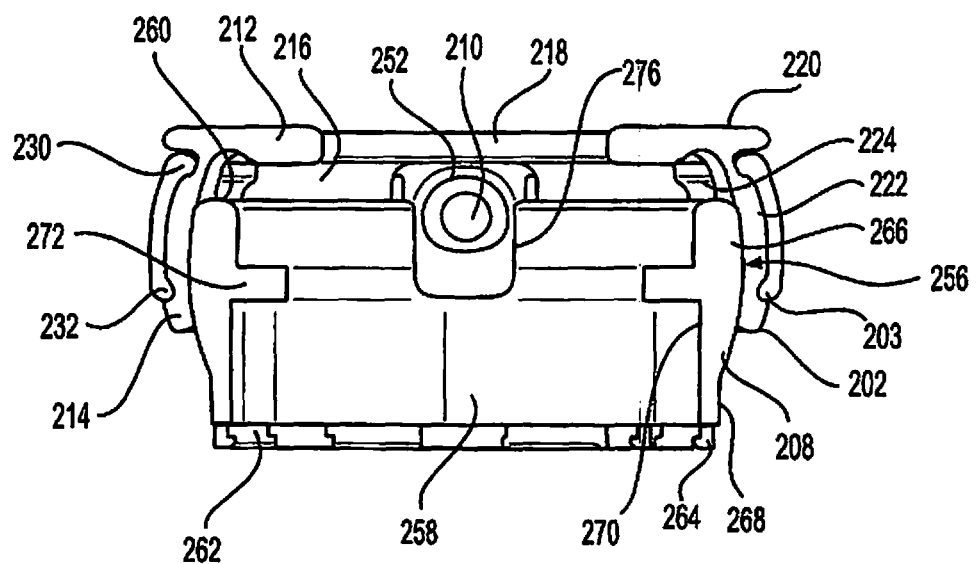
FIG. 2B illustrates a cross-sectional view of a polyaxial endplate assembly as described herein.

As illustrated in FIG. 2B, the articulable plate member 202 can include a plate portion 212 and a rounded body portion 214. The body portion 214 can define a cavity 216 therein. The plate portion 212 can include an aperture 218 extending therethrough. The plate portion 212 may include an outer surface 220 having various topographical features. For example, in some embodiments the outer surface 220 of the plate portion 212 can be planar; in other embodiments, it can be convex. In yet other embodiments, it can be concave. Additionally, the outer surface 220 may include one or more features to enhance the engagement or friction between the implant and a vertebral body or other bone feature. For example, the outer surface 220 can be roughened, and can include, for example, a plurality of teeth, bumps, peaks, grooves, and/or knurling. The outer surface 220 can include at least one engagement member. The engagement member can be configured to engage and/or apply force to a vertebral body. For example, the engagement member can be a spike. In some embodiments, the outer surface 220 can include a plurality of engagement members. The engagement member(s) can advantageously prevent sliding or other translational movement of the assembly after installation within the vertebral space. In other embodiments, the outer surface 220 can include an imaging member, such as one or more radiographic markers.

The body portion 214 of the articulable plate member 202 can include a plurality of tabs 222, as illustrated in FIG. 2B. The tabs 222 can be separated by a plurality of slots 224. The number of tabs 222 making up the body portion 214 can vary, and can be, for example, in the range of from about two to about twelve. In some embodiments, the tabs 222 and slots 224 may be equally sized and spaced. In other embodiments, the tabs 222 and/or slots 224 may have variable sizes. Advantageously, the body portion 214 may be compressible, bendable, flexible, and/or constrictable (e.g., a force may be applied to the tabs 222 which causes the tabs 222 to flex inward, thereby reducing the volume of the cavity 216).

Figure 2C:
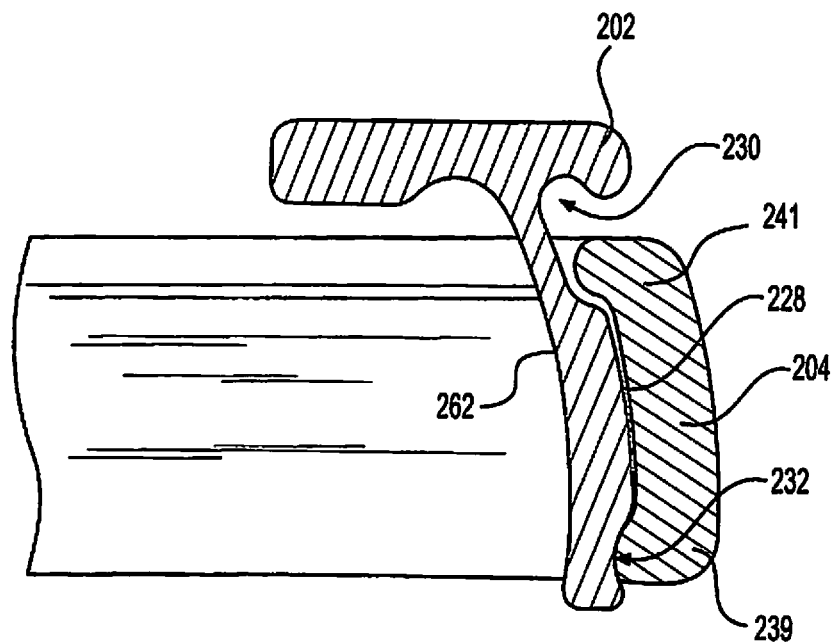
FIG. 2C illustrates a cross-sectional view of a clamp assembly engaging an articulable plate member as described herein.

The body portion 214 may be rounded. For example, as illustrated in FIG. 2C, the body portion 214 can include an inner surface 226 and an outer surface 228, one or both of which may be curved (e.g., may include an at least partially curved longitudinal cross section). Additionally, the outer surface 228 may include one, two, or more circumferential grooves, such as top groove 230 and bottom groove 232. The top and bottom grooves 230 and 232 may have the same or different dimensions (e.g., height and/or depth). For example, the bottom groove 232 may have a depth that is less than that of the top groove 230. In some embodiments, the top and bottom grooves 230, 232 may be configured to engage corresponding circumferential projections on an inner surface of a clamp member, as described herein.

Figure 2D:
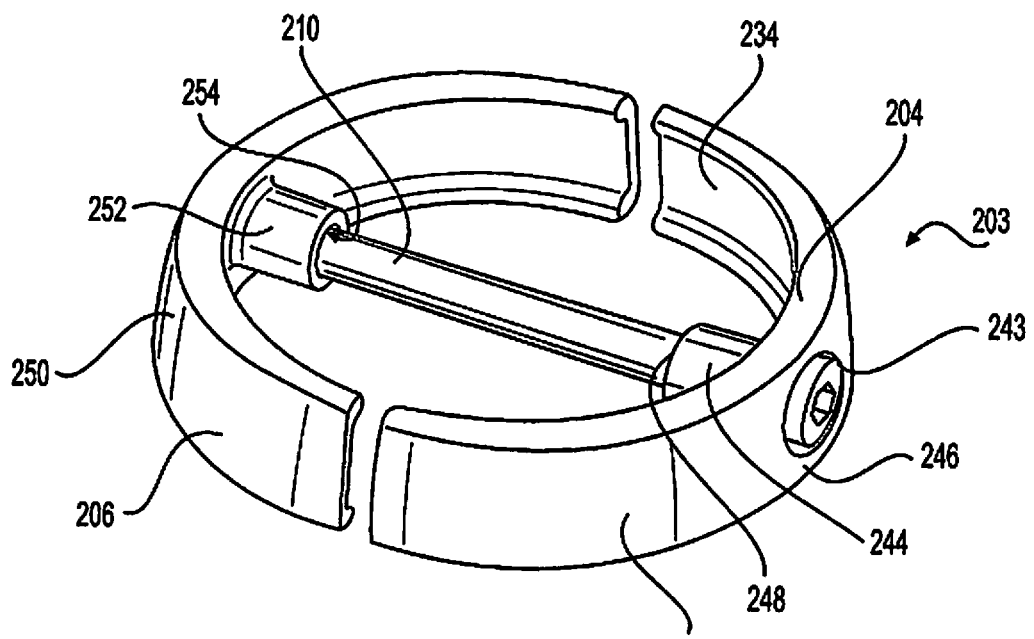
FIG. 2D illustrates a perspective view of a clamp assembly as described herein.

As illustrated in FIG. 2D, the clamp assembly 203 can include first and second clamp members 204, 206 and securing element 210. The first and second clamp members 204, 206 each can include a body having generally C-shaped transverse cross section, and when assembled, can form a collar around the articulable plate member 202. Except as otherwise described herein, the second clamp member 206 may share some or all of the same features as the first clamp member 204. First clamp member 204, also referred to herein as the front clamp member, can include an inner surface 234 and an outer surface 236. In some embodiments, the inner surface 234 may have a transverse cross section in the shape of a circular segment. In other embodiments, the inner surface 234 may have a transverse cross section in the shape of an elliptical segment. The outer surface 236 may also have a transverse cross section in the shape of either a circular or elliptical segment. In some embodiments, the inner surface 234 can have an elliptical transverse cross section and the outer surface 236 can have a circular transverse cross section. The body of the first clamp member 204 may have a variable thickness, as measured between the inner and outer surfaces 234, 236. For example, as illustrated in FIG. 2A, the first clamp member 204 may have a thickness at each end 238, 240 that is less than a thickness at the center portion 242. Consequently, the thinner end portions 238, 240 may be more flexible than the thicker center portion 242. The inner and outer diameters of the first clamp member 204 may also vary. For example, in some embodiments, the inner diameter of the first clamp member 204 may be less than an outer diameter of the body portion 214 of the articulable plate member 202. However, the first clamp member 204 may still be able to encompass the body portion 214 due to the flexibility of the thinner end portions 238, 240. Those skilled in the art may thus appreciate that this discrepancy in diameters and/or the variable thickness of the clamp members may advantageously increase or augment the clamping pressure applied by the clamp assembly 203 and may promote or enable uniform distribution of clamping pressure about the circumference thereof.

The first and second clamp members 204, 206 may also include inner and/or outer curved longitudinal cross sections, as illustrated in FIG. 2C. The inner surface 234 can be configured to engage the articulable plate member 202. Accordingly, the inner surface 234 may include one or more features to enhance engagement between these two members. For example, the inner surface 234 can include a first circumferential protrusion or lip 239 at a bottom end of the first clamp member 204. As illustrated in FIG. 2C, the circumferential protrusion 239 may be configured to engage and apply pressure to the bottom groove 232 of the articulable plate member 202. The application of localized force near the bottom of the articulable plate member 202 may advantageously increase the clamping strength and efficiency of the clamp assembly 203, as compared to the even distribution of force along the inner surface 234. The inner surface 234 may also include a second circumferential protrusion or lip 241, which may be positioned near a top end of the first clamp member 204. The second circumferential protrusion or lip 241 may also be configured to engage a groove of the articulable plate member 202, and may, for example, assist or promote alignment of the first clamp member 204 relative to the articulable plate member 202.

The first clamp member 204 can also include a central receptacle 243, as illustrated in FIG. 2D. A central protrusion, such as boss member 244, may also extend or protrude from the interior surface 234. The central receptacle 242 may pass through a body portion 246 of the first clamp member 204 and the boss member 244. As illustrated in FIG. 2D, the central receptacle may pass completely through from the outer surface 236 of the body 246 to the inner surface 248 of the boss member 244. The central receptacle 243 may be configured to receive and engage the securing element 210 therein. In some embodiments, the central receptacle 243 may include a threaded section and/or may be entirely threaded. In some embodiments, the central receptacle 243 may have a constant inner diameter. In other embodiments, the central receptacle 243 may include an enlarged diameter portion adjacent the outer surface 236 that can be configured to accommodate an enlarged head of a set screw or other type of securing element 210.

The second clamp member 206, also referred to as the back clamp member, can also include a body 250 and a boss member 252 or other central protrusion through which a central receptacle 254 may pass, as illustrated in FIG. 2D. The central receptacle 254 may also be configured to receive and/or engage the securing element 210 therein. When in an assembled configuration, as illustrated in FIG. 2D, those skilled in the art may appreciate that the axes of central receptacles 242, 254 may be aligned such that the securing element 210 may be first inserted (e.g., threaded) into the first, front clamp member 204 and subsequently into the second, back clamp member 206 in a straight line. The central receptacle 254 may include at least some of the same features as the central receptacle 242. For example, the central receptacle 254 may be at least partially threaded. In some embodiments, the central receptacle 254 may include one or more unique features. For example, the central receptacle 254 may not pass entirely through the body 250 to an outer surface of the second clamp member 206. Additionally, the central receptacle 254 may be configured to receive a shank, but not an enlarged head, of a set screw or other securing element 210.

As described herein, the securing element 210 may be configured to be received within and/or engage with the central receptacles 243, 254 of the first and second clamp members 204, 206. In some embodiments, the securing element 210 may be threaded into the central receptacles 243, 254, for example, when the securing element 210 is a set screw or a threaded rod. In some embodiments, the securing element 210 may be a set screw that can include a head having a tool-receiving receptacle and a threaded shank. The head may have a diameter that is equal to or larger than a major diameter of the threaded shank. In use, the securing element 210 can be threaded into or otherwise engaged with the first clamp member 204 and then into the second clamp member 206. As illustrated in FIG. 2A, the first and second clamp members 204, 206 can be separated by a gap 278. As the securing element 210 continues to be threaded into the first and second clamp members 204, 206, it can pull the first and second clamp members 204, 206 together, thereby exerting a clamping force on the articulable plate member 202. Thus, the securing element 210 can advantageously be used to stabilize an orientation (e.g., an angle) of the articulable plate member 202 relative to the receiving member 208.

As illustrated in FIG. 2B, the receiving member 208 can include a rounded portion 266 having a convex exterior surface 256 and a rounded or curved longitudinal cross section. The receiving member 208 can also include a cylindrical portion 268 extending proximally therefrom. The receiving member 208 may be generally annular or hollow and can include a passageway 258 extending axially from a distal end surface 260 to a proximal end surface 262. The rounded portion 266 can include an axially-variable thickness, as measured between outer surface 256 and inner surface 270. The cylindrical portion 268 can have a constant thickness. At least a portion of the receiving member 208 may be configured to be received within the cavity 216 of the body portion 214 of the articulable plate member 202, and at least a portion of the exterior surface 256 may be configured to contact or engage the inner surface 226 of the body portion 214. In some embodiments, the rounded portion 266 of the receiving member 208 can additionally include a ledge 272 extending along and/or protruding from at least a portion of the interior surface 270. The distal end surface 260 can also include at least one axial pocket or slot 274, as illustrated in FIG. 2A. As illustrated in FIGS. 2A-B, the receiving member 208 can include two slots 274, 276. As illustrated in FIG. 2A, the two slots may be oriented approximately 180 degrees apart from each other. The two slots 274, 276 may be configured to receive the boss members 244, 252 of the first and second clamp members 204, 206 therein. Advantageously, the slots 274, 276 may entrap, constrain, or restrain the boss members 244, 252 and reduce spinning or rotating of the clamp assembly 203 relative to the receiving member 208.

In some embodiments, the receiving member 208 can include one or more coupling elements 264. The coupling element 264 can be configured to couple or engage the polyaxial endplate assembly 200 with a vertebral implant, such as those described in U.S. Publication No. 2011/0251691 to McLaughlin et al. As illustrated in FIG. 2B, in some embodiments, the coupling element 264 can include a projection member, such as a tab, extending from the proximal end surface 262. As further illustrated in FIG. 2B, the projection member or tab can include a protrusion, such as a head or a hook that can be configured to be received within a groove or undercut in the vertebral implant. In other embodiments, the coupling element 264 can be a groove or slot configured to receive a portion of the vertebral implant therein. As illustrated in FIG. 2B, the receiving member 208 can include a plurality of coupling elements 264.

In some embodiments, the receiving member 208 may optionally include a neck portion (not shown) which can extend from the proximal end 262. The neck portion can include a hollow cylinder (having e.g., constant inner and outer diameters) in fluid communication and coaxial with the passageway 258. The receiving member 208 can have an outer diameter that is greater than an outer diameter of the neck portion. In some embodiments, the neck portion may be configured to be received within a vertebral implant as part of the coupling process.

Some embodiments herein are directed to methods of installing a vertebral implant assembly that can include a vertebral implant and a first (e.g., superior or inferior) polyaxial assembly, such as the polyaxial endplate assembly 200. These methods can include providing the first polyaxial endplate assembly 200 in an unassembled, partially assembled, or fully assembled state. In some embodiments where the first polyaxial endplate assembly 200 is partially or fully assembled, some or all of the components of the assembly 200 may be coupled or connected, but some or all of the components may still be capable of rotating, pivoting, and/or translating relative to one another.

Some embodiments can include providing the first polyaxial endplate 200 in an assembled state. In these embodiments, the rounded portion 266 of the receiving member 208 may be at least partially disposed or nested within the cavity 216 of the articulable plate member 202, for example, by snapping the articulable plate member 202 over the receiving member 208. The clamp assembly 203 may be engaged with the body portion 214 of the articulable plate member 202, for example, by positioning the first and second clamp members 204, 206 around the articulable plate member 202 and inserting the securing member 210 therethrough via central receptacle 243. The step of positioning the first and second clamp members 204, 206 around the articulable plate member 202 may further include inserting the boss members 244, 252 into the slots 274, 276 on the receiving member 208. Those skilled in the art may appreciate that in the assembled state, the articulable plate member 202 may be able to articulate or pivot relative to the receiving member 208 and/or the locking assembly 203.

The method can also include providing a vertebral implant that can include a first (e.g., superior) engagement member and/or a second (e.g., inferior) engagement member. The vertebral implant can be, for example, a corpectomy implant, an interbody implant, a vertebral body replacement, a cage, or a spacer. In some embodiments, the vertebral implant can have a variable and/or adjustable height. In some embodiments the vertebral implant may be a vertically-expandable or extendable implant described in U.S. Publication No. 2011/0251691 to McLaughlin et al. Those skilled in the art may appreciate that the polyaxial endplate assemblies described herein may be used instead of the endplates described in the aforementioned publication.

The superior engagement member of the vertebral implant can include a coupling element extending from a superior surface. The inferior engagement member can include a coupling element extending from an inferior surface. With regards to either the superior and/or inferior engagement members the coupling element may be, for example, a tab, notch and/or socket. In some embodiments, the superior and/or inferior engagement member(s) can include a plurality of tabs. In other embodiments, the superior and/or inferior engagement member(s) can include a plurality of notches.

The method can also include coupling a first (e.g., superior) polyaxial endplate assembly 200 with the first (e.g., superior) engagement member. In these embodiments, the receiving member 208 can include coupling element 264 (e.g., tab and/or notch) extending from proximal end 262. As described herein, the receiving member 208 can include a plurality of coupling elements 264. The step of coupling the first polyaxial endplate assembly with the first engagement member can include engaging the coupling element 264 of the receiving member 208 with the coupling element of the first engagement member. For example, this step can include interdigitating or dovetailing the coupling element 264 of the receiving member 208 (e.g., a tab or notch) with the coupling element of the first engagement member (e.g., a notch or tab). In some embodiments, the coupling element 264 can be a projection member that includes a protrusion, and the first engagement member can be an undercut in the vertebral implant. In these embodiments, the coupling step can include snapping the protrusion into the undercut, for example by applying pressure to momentarily deflect, flex, or bend the coupling element 264 outwards and allowing the protrusion to be received within the undercut when the coupling element 264 returns to a neutral position.

In some embodiments, the receiving member 208 can additionally include a cylindrical neck portion. In these embodiments, the step of coupling the first polyaxial endplate assembly with the first engagement member can include inserting the cylindrical neck portion into the socket of the vertebral implant.

The method can also include coupling a second (e.g., inferior) polyaxial endplate assembly with the second (e.g., inferior) engagement member. This step can be performed in substantially the same way as the coupling of the first polyaxial endplate assembly with the first engagement member. Those skilled in the art may appreciate that in some embodiments only one polyaxial endplate assembly may be used (e.g., inferior or superior), while in other embodiments two polyaxial endplate assemblies may be used (e.g., inferior and superior). Additionally, those skilled in the art may appreciate that steps described herein with respect to the first polyaxial endplate assembly can also be applied to installation of the second polyaxial endplate assembly.

Upon assembly, the method can also include inserting the vertebral implant assembly into a selected location, such as a cavity between two vertebral bodies created by a corpectomy or other procedure. In embodiments using an expandable vertebral implant, this step can additionally include expanding the vertebral implant from a first height to a second height, e.g., until the polyaxial endplate assembly contacts the vertebral body. Advantageously, those skilled in the art may appreciate that the articulable plate member of the vertebral implant assembly may be configured to pivot or articulate relative to the assembly, even after being put together. Accordingly, the angles of the polyaxial endplate assembly may be adjusted in situ to correspond to the topography of the adjacent vertebral body.

The method can also include applying a force to the first articulable plate member 202 to stabilize an orientation of the first articulable plate member 202 relative to the vertebral implant. This step can include constricting and/or compressing the first and second clamp members 204, 206 around the body portion 214 of the first articulable plate member 202. The first and second clamp members 204, 206 may be constricted by engaging the securing element 210 therewith. As described herein, in embodiments where the securing element 210 is a set screw and the first and second clamp members 204, 206 include threaded central receptacles, as the set screw is threaded into the central receptacles 243, 254, the set screw may effectively compress or pull the first and second clamp members 204, 206 together. Those skilled in the art may appreciate that when the body portion 214 is constricted, squeezed, and/or compressed, the tabs 222 may flex inward in enhanced frictional engagement with the receiving member 208, thereby locking, stabilizing, and/or securing the orientation (e.g., angle) of the first articulable plate member 202 relative to the vertebral implant assembly. When in the locked, stabilized, and/or secured configuration, the first articulable plate member 202 may be effectively unable to pivot, articulate, and/or rotate relative to the first clamping assembly 203 and/or the first receiving member 208.

As described herein, polyaxial endplate assemblies may advantageously be used in combination with vertebral implants to enable or promote a customized, adjustable fit between vertebral bodies. Regardless, in use, a vertebral implant assembly kit may include a number of interchangeable endplate assemblies and vertebral implants having varying characteristics (e.g., height, endplate dimensions, and angulation) configured to fit a wide variety of individuals. To select the appropriate combination of endplate assemblies and vertebral body, a surgeon or other practitioner may measure various parameters of the intervertebral space. This may be done intraoperatively using a physical measurement tool, such as a ruler or caliper, and/or preoperatively using software in combination with imaging techniques such as x-ray, CT or MRI. In some instances, different methods may be used to measure different characteristics. For example, height and footprint (e.g., width) may be measured physically and angulation may be measured using imaging. In addition to being potentially time-consuming, there may be issues with these methods that limit their accuracy. For example, height of the intervertebral space can be difficult to measure physically, as caliper devices may not fit within the operative area or may be obstructed by nearby anatomy, and generally may not be the same shape as the vertebral implant assembly. Additionally, caliper devices may not be able to exert force sufficient to restore height and/or alignment to collapsed spinal segments, and may therefore not be able to realistically measure the appropriate dimensions for the vertebral implant assembly. Imaging can also have limitations. For example, preoperative images of the spine may not reflect the actual dimensions needed for a vertebral implant assembly. Accordingly, described herein are vertebral endplate trial devices that can measure footprint, angulation, and height all in one step, thus saving time over other methods that may require multiple measurement techniques. As described further herein, the endplate trials may be configured to exert force on the vertebral bodies and/or restore height to collapsed segments, and may therefore provide a more accurate determination of the appropriate dimensions for the vertebral implant assembly. Once inserted, x-rays or other images may be taken in situ to confirm fit.

Turning now to FIGS. 3A-10, endplate trials are illustrated in accordance with embodiments described herein. The endplate trial can include a top surface, a bottom surface, and a side surface therebetween. Those skilled in the art may appreciate that the directional terms used herein, such as "top," "bottom," "side," "front," "back," and the like are used for descriptive purposes and do not necessarily limit the orientation(s) in which the endplate trials may be used. For example, the endplate trials described herein may be configured to engage either a superior or inferior vertebral surface. Additionally, the endplate trial can include a coupling element configured to reversibly engage a vertebral implant device (e.g., a device for use in a vertebral implant procedure). Any suitable vertebral implant device may be used. For example, the vertebral implant device may be a vertebral trial, such as those described in U.S. Publication No. 2012/0232660 to Davenport, entitled EXPANDABLE TRIAL ASSEMBLY FOR EXPANDABLE VERTEBRAL IMPLANT, which is hereby incorporated by reference herein in its entirety. In other embodiments, the vertebral implant device may be a vertebral prosthesis, such as, without limitation, a cage, spacer, vertebral body replacement, interbody implant, or expandable vertebral implant as described in U.S. Publication No. 2011/0251691 and/or U.S. Publication No. 2012/0232660.

Figure 3A:
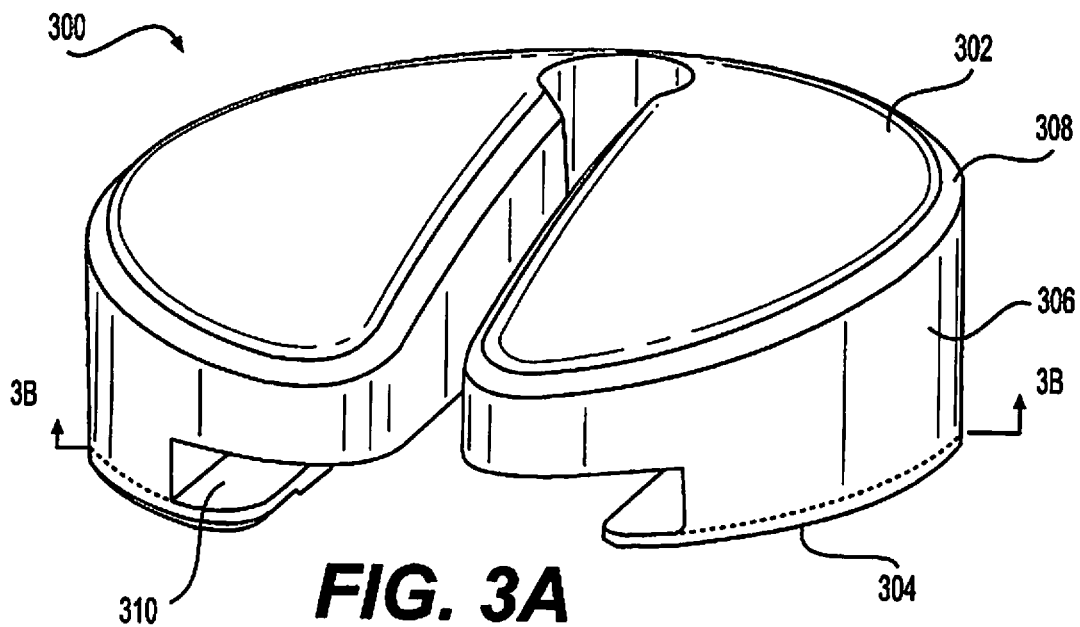
FIG. 3A illustrates a perspective view of an endplate trial as described herein.

FIGS. 3A-F illustrate endplate trial 300. As illustrated in FIG. 3A, endplate trial 300 can include a top surface 302, bottom surface 304, and side surface 306 therebetween. Endplate trial 300 may also include a chamfered edge 308 between the side surface 306 and the top and/or bottom surfaces 302, 304. The top surface 302 may be configured to engage (e.g., contact and/or apply force to) a vertebral body. For example, the top surface 302 may have a curvature, as viewed from the side surface, selected from convex, concave, and planar. The bottom surface 304 may also have a curvature, as viewed from the side surface, selected from convex, concave, and planar. Additionally, endplate trial 300 may have a height, as measured between the top surface 302 and bottom surface 304, which varies along a length or width thereof. The shape of the endplate trial 300, as viewed from the top and/or bottom surface 302, 304, may also vary. For example, the endplate trial 300 may have a shape selected from circular, elliptical, square, trapezoidal, rectangular, and kidney-shaped.

As described herein, the endplate trial may advantageously include a coupling element configured to reversibly engage the endplate trial with a vertebral implant device. In some embodiments, the coupling element may be configured to slideably receive at least a portion of the vertebral implant device therein. For example, the coupling element may be an undercut, such as lateral undercut 310, as illustrated in FIG. 3A.

Figure 3B:
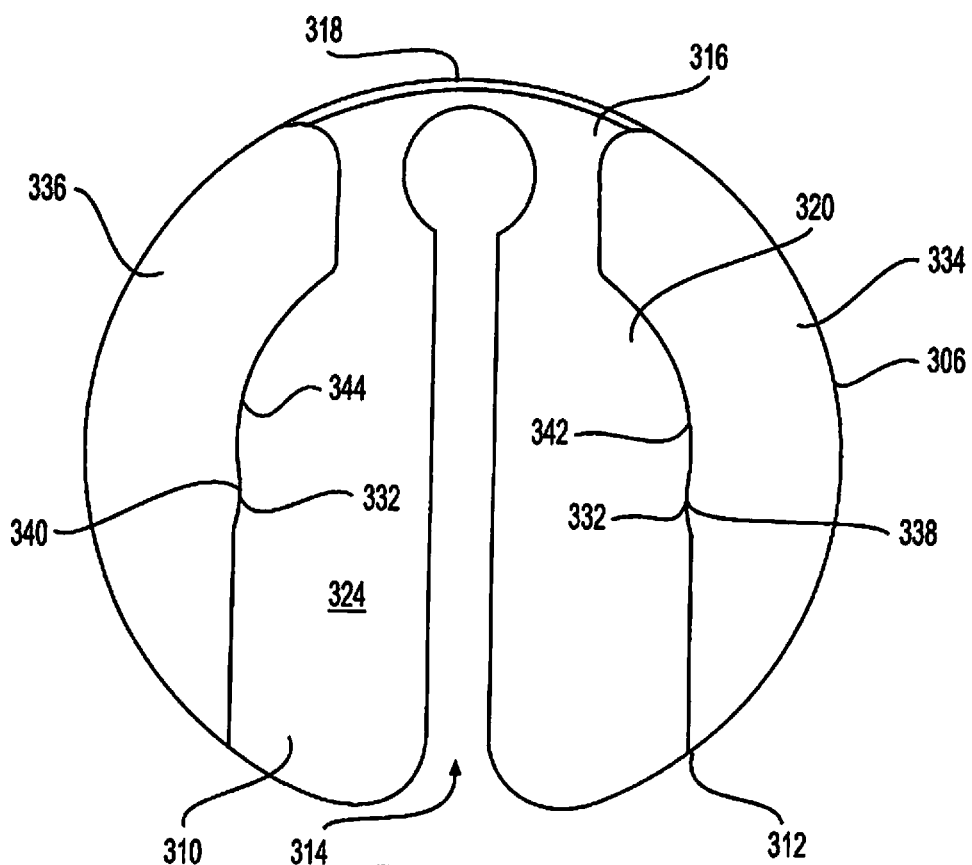
FIG. 3B illustrates a cross-sectional view of an endplate trial as described herein.

As illustrated in FIG. 3B, the lateral undercut 310 can include a first or front opening 312 on the side surface 306 of the endplate trial 300. The front opening 312 may be located at a first or front end 314 of the endplate trial 300 and may have a width greater than a width of the portion of the vertebral implant device to be received within the lateral undercut 310. The lateral undercut 310 may further include a second or back opening 316 on the side surface 306 at a second or back end 318 of the endplate trial 300. Thus, in some embodiments, the lateral undercut 310 may pass entirely through the endplate trial 300 from one section of the side surface 306 to another section of the side surface 306. In other embodiments, the lateral undercut 310 may pass only partially through the endplate trial 300. Additionally, the lateral undercut 310 may define an inner surface 324 of the endplate trial. The second or back opening 316 may have a width that is less than the width of the portion of the vertebral implant device to be received within the lateral undercut 310. The lateral undercut 310 can additionally include a rounded cavity 320 between the front opening 312 and the back opening 316. The rounded cavity 320 may have a diameter that is greater than the width of the back opening 316. The lateral undercut 310 may also include a transition area 322 between the rounded cavity 320 and the front opening 312. The transition area 322 may advantageously be configured to have a width that is less than a width of the portion of the vertebral implant device to be received within the lateral undercut 310. Conversely, the transition area 322 may define first and second protrusions 338, 340 on inner side walls 342, 344 of the endplate trial 300, as illustrated in FIG. 3B.

Figure 3C:
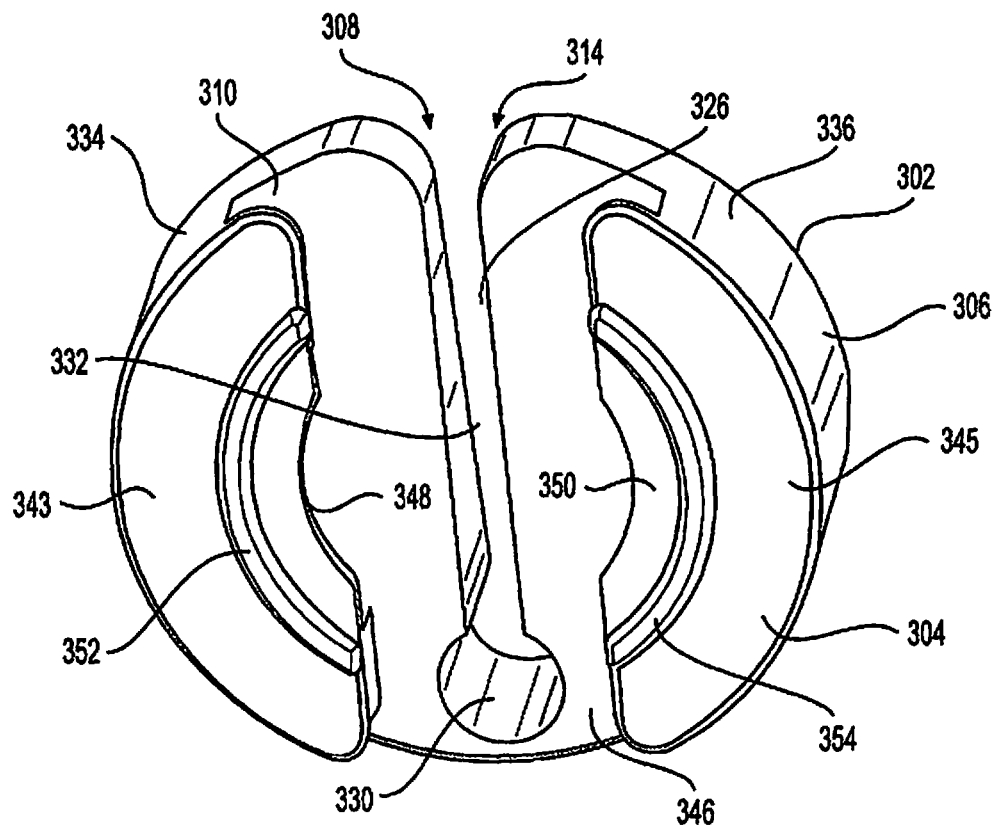
FIG. 3C illustrates a perspective view of an endplate trial as described herein.

The endplate trial may additionally include a retaining element. The retaining element may be configured to retain the portion of the vertebral implant device in engagement with the coupling element (e.g., within the rounded cavity 320). In some embodiments, the retaining element may include a spring element. The spring element may include first and second deflectable members, wherein each deflectable member includes a protrusion configured to engage the vertebral implant device. As illustrated in FIG. 3C, in some embodiments the retaining element may include a vertical slot 326. As illustrated in FIGS. 3B-C, the vertical slot 326 may be in fluid communication with, overlap, and/or extend parallel to the lateral undercut 310. The vertical slot 326 can have a depth that extends entirely through the endplate trial from the top surface 302 to the bottom surface 304. The vertical slot 326 may also have a first end that includes an opening 328, a second end that includes a rounded terminus 330, and an elongate void 332 therebetween. As illustrated in FIG. 3C, the opening 328 may be located adjacent the front end 314 of the endplate trial 300 and may pass through the side surface 306.

As illustrated in FIG. 3C, the vertical slot 326 may divide the endplate trial 300 into first and second deflectable sections 334, 336. The first and second deflectable sections 334, 336 may be flexibly connected, e.g., may be configured to bend, flex, deflect, and/or pivot relative to each other. The vertical slot 326 may have a width as defined by the distance between the first and second deflectable sections 334, 336. As illustrated in FIG. 3C, the width of the vertical slot 326 may vary, and in some embodiments the vertical slot 326 can include a constant width section (e.g., corresponding to the elongate void 332) and a variable width section (e.g., corresponding to the rounded terminus 330). Additionally, the maximum width or diameter of the rounded terminus 330 may be greater than the width of the elongate void 332. Advantageously, the relatively wide rounded terminus 330 may contribute to the spring mechanism of the endplate trial 300 by encouraging and/or promoting the first and second deflectable sections 334, 336 to bend or deflect, and/or by enhancing their range of motion.

Figure 3D:
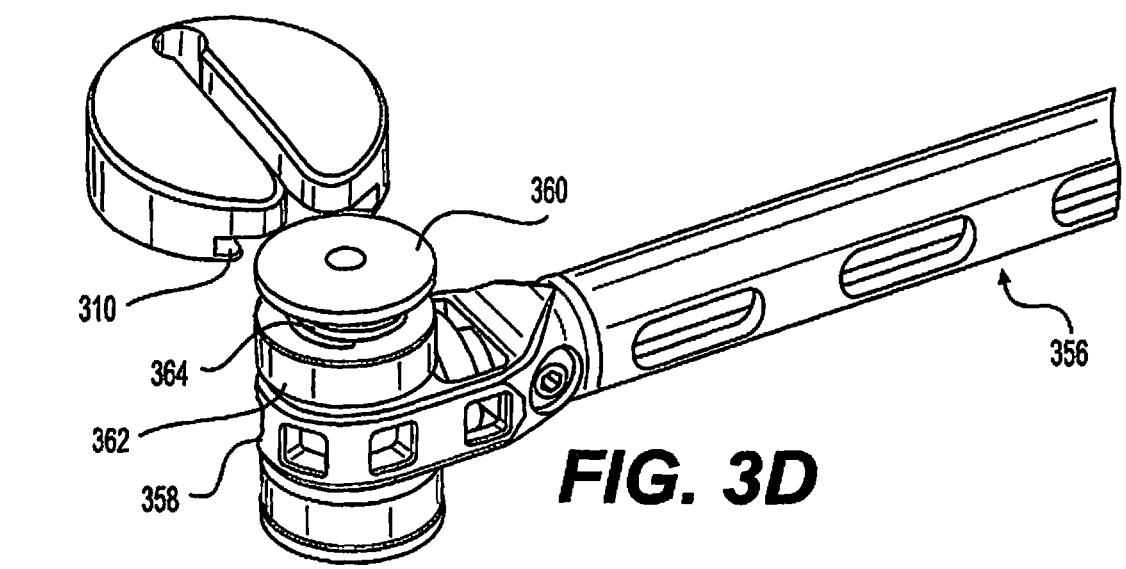
FIG. 3D illustrates an endplate trial and an expandable trial assembly as described herein.
Figure 3E:
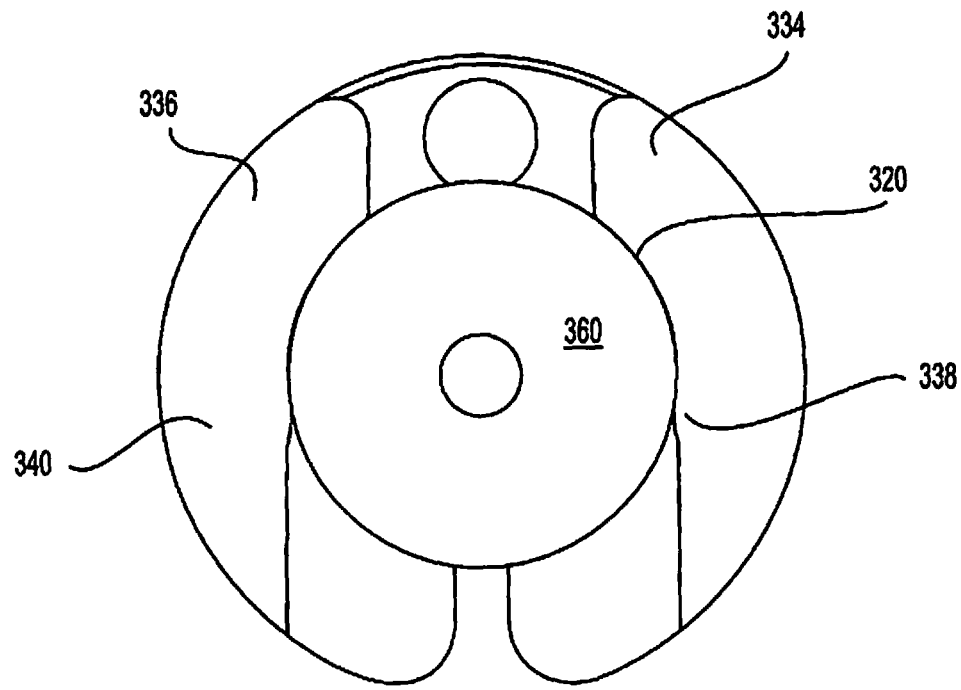
FIG. 3E illustrates a cross-sectional view of an endplate trial engaged with an expandable trial assembly as described herein.

In use, the endplate trial 300 may be configured to be engaged or coupled with a tip of an implant trial assembly, for example, implant trial assembly 356 illustrated in FIG. 3D. Implant trial assembly 356 can include an expandable tip assembly 358 that includes a generally disc-shaped endplate 360. In these embodiments, the disc 360 of the implant trial assembly tip 358 may be laterally inserted (e.g., slid) into the lateral undercut 310. As the widest part of the disc 360 enters the narrow transition area 332, the disc 360 contacts the protrusions 338, 340 and causes the first and second deflectable sections 334, 336 to deflect or splay outwards. As the first and second deflectable sections 334, 336 splay apart, the width of the transition area 322 temporarily expands, thereby allowing the disc 360 to pass through to the rounded cavity 320. Once pressure is released from the protrusions 338, 340, the deflectable sections 334, 336 return or spring back to their neutral orientation, thereby trapping or retaining the disc 360 within the rounded cavity 320, as illustrated in FIG. 3E.

The bottom surface 304 of the endplate trial 300 is illustrated, for example, in FIG. 3C. As illustrated therein, the bottom surface 304 may be divided into first and second sections 343, 345 separated by a gap 346. The gap 346 may include one or more straight (e.g., linear) sections and one or more curved sections. Conversely, the first and second bottom sections 343, 345 may each include a curved or partially circular cutout 348, 350. The cutouts 348, 350 may be configured to receive a portion of the vertebral implant device therein (e.g., cylindrical body 364 of expandable trial assembly 356, as illustrated in FIG. 3D).

Figure 3F:
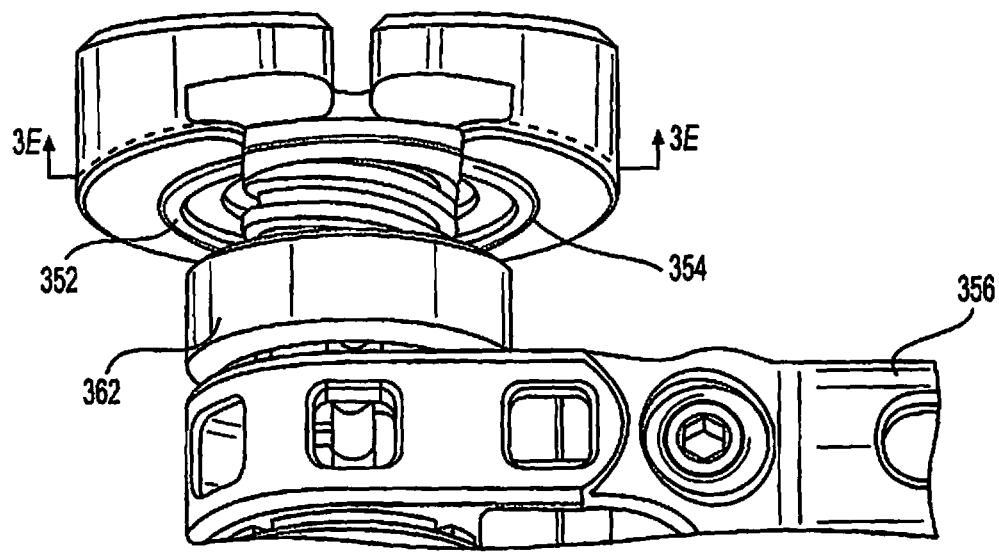
FIG. 3F illustrates a perspective view of an endplate trial engaged with an expandable trial assembly as described herein.

In some embodiments, the endplate trial may also include one or more stabilizing members. The stabilizing member may be configured to engage at least a portion of the vertebral implant device, for example, only when the device is in a particular configuration. For instance, the expandable tip assembly 358 of expandable trial assembly 356, illustrated in FIG. 3D, may be configured to transition reversibly between an expanded configuration and a contracted configuration. In these embodiments, the stabilizing member may be configured to engage at least a portion of the expandable tip assembly 358 when the expandable trial assembly 356 is in the contracted configuration. Advantageously, in providing additional engagement between the endplate trial and the vertebral implant device, the stabilizing member may inhibit the inadvertent removal or release of the endplate trial from the vertebral implant device. In some embodiments, the stabilizing member may include one or more protrusions or projections on a bottom surface of the endplate trial. As illustrated in FIG. 3C, the first and second bottom sections 343, 345 of the endplate trial 300 may each include a projection 352, 354 extending therefrom. The projection(s) may have a variety of shapes, such as round, circular, square, rectangular, pentagonal, and annular, and may include rounded corners and/or edges. As illustrated in FIG. 3C, the projections 352, 354 may each take the shape of a circular or curved ring segment. Together, the projections 352, 354 may form a partial circle or oval. The width or diameter of the partial circle or oval may vary depending on the dimensions of the vertebral implant device with which the endplate trial 300 may be engaged. In some embodiments, the partial circle or oval may be configured to at least partially surround a portion of expandable trial assembly 356, as illustrated in FIG. 3F. For example, the circular ring segments 352, 354 may be spaced apart by a maximum distance that is greater than a diameter of a gear member 362 of the expandable trial assembly 356.

Figure 4A:
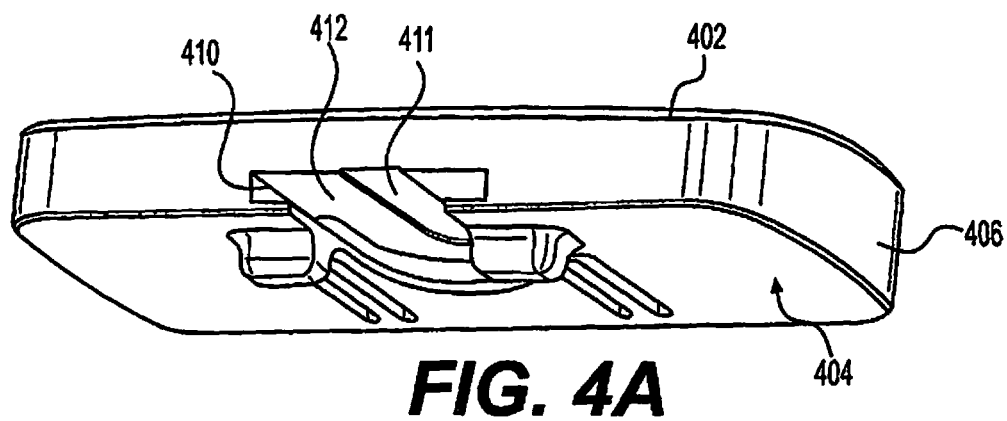
FIG. 4A illustrates a perspective view of an endplate trial as described herein.
Figure 4B:
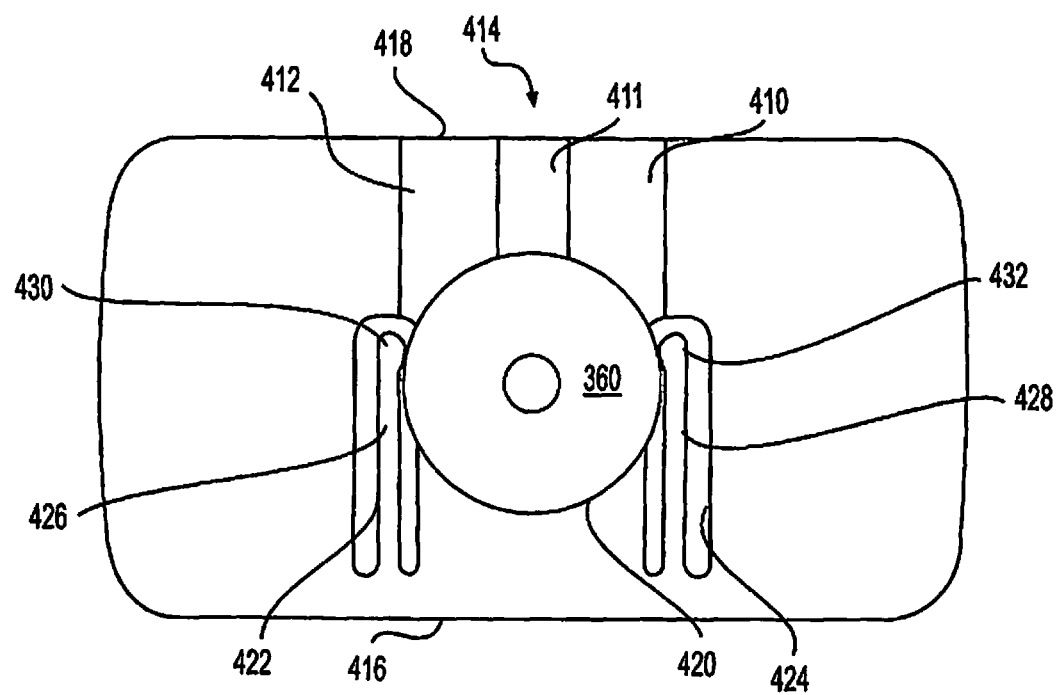
FIG. 4B illustrates a cross-sectional view of an endplate trial engaged with an expandable trial assembly as described herein.

Turning to FIG. 4A-D, endplate trial 400 is illustrated in accordance with embodiments described herein. Unless otherwise described herein, endplate trial 400 may include some or all of the same features as described with respect to endplate trial 300. As illustrated in FIG. 4A, endplate trial 400 may include a top surface 402, bottom surface 404, and side surface 406 therebetween. Endplate trial 400 may also include a coupling element configured to reversibly engage at least a portion of a vertebral implant device (e.g., expandable trial assembly 356). The coupling element of endplate trial 400 may include a lateral undercut 410. The lateral undercut 410 may pass partially or completely through the endplate trial 400 (e.g., between a front end 414 and a back end 416, illustrated in FIG. 4B). For example, as illustrated in FIG. 4B, the lateral undercut 410 may include a first or front opening 418 and a rounded cavity 420. Additionally, lateral undercut 410 may define an inner surface 412 of the endplate trial 400. In some embodiments, the endplate trial 400 can further include a groove 411 on the inner surface 412 that can extend along a length of the lateral undercut 410, as illustrated in FIGS. 4A-B. The groove 411 may advantageously encourage sliding of the vertebral implant device within the lateral undercut 410.

Endplate trial 400 may additionally include a retaining element. As illustrated in FIG. 4B, the retaining element can include a first or left vertical slot 422 and a second or right vertical slot 424. Each of these vertical slots may extend entirely through the endplate trial 400 from the top surface 402 to the bottom surface 404. As illustrated in FIG. 4B, each of the vertical slots 422, 424 may be generally U-shaped as viewed from the top and bottom surfaces 402, 404 and may define first and second (e.g., left and right) deflectable arms 426, 428. The first and second deflectable arms 426, 428 may each include a protrusion or prong 430, 432 that protrudes into the lateral undercut 410.

Figure 4C:
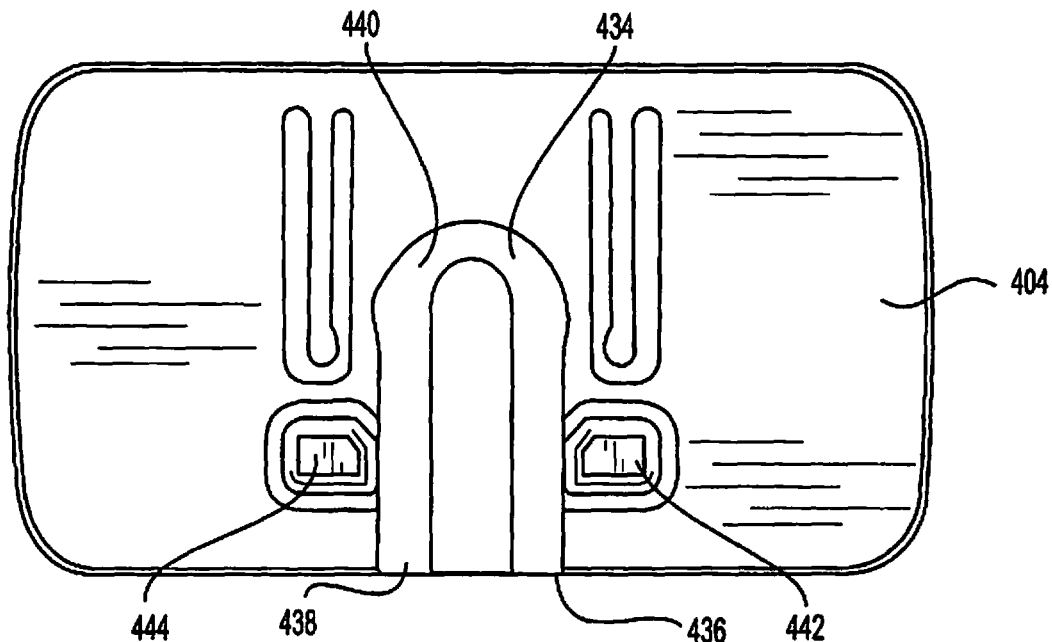
FIG. 4C illustrates a perspective bottom view of an endplate trial as described herein.
Figure 4D:
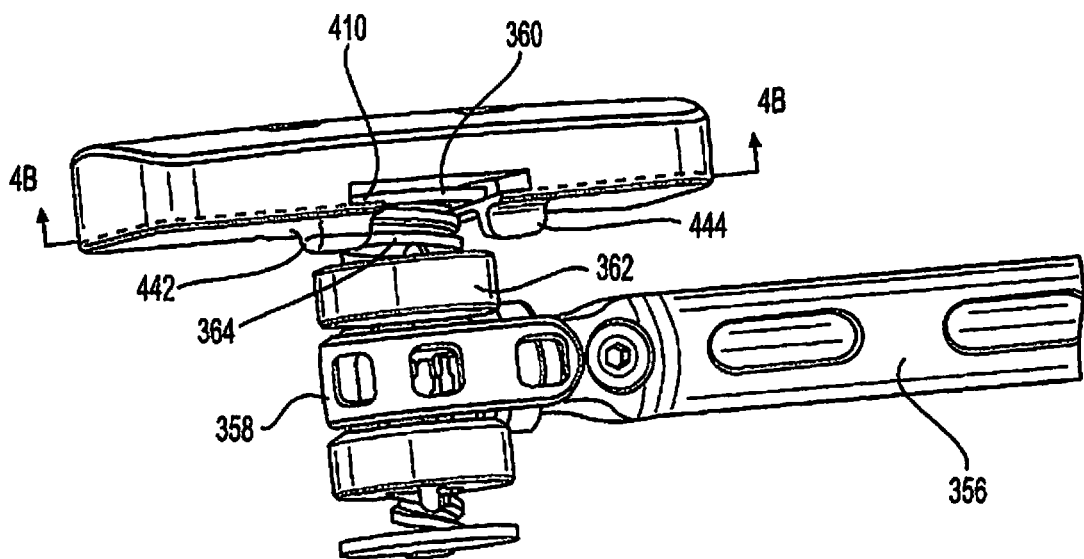
FIG. 4D illustrates a perspective view of an endplate trial engaged with an expandable trial assembly as described herein.

In use, the endplate trial 404 may be configured to be engaged or coupled with a tip of an implant trial assembly, for example, implant trial assembly 356 illustrated in FIG. 4D. As described herein, implant trial assembly 356 can include an expandable tip assembly 358 that includes a generally disc-shaped endplate 360. In these embodiments, the disc 360 may be laterally inserted (e.g., slid) into the lateral undercut 410. As the widest part of the disc 360 contacts or applies force to the protrusions 430, 432, it causes first and second deflectable arms 426, 428 to deflect or splay outwards. As the first and second deflectable arms 426, 428 splay apart, the width of the lateral undercut 410 temporarily expands, thereby allowing the disc 360 to pass through to the rounded cavity 420. Once pressure is released from the protrusions 430, 432, the deflectable arms 426, 428 may return or spring back to their neutral position, thereby trapping or retaining the disc 360 within the rounded cavity 420, as illustrated in FIGS. 4B and 4D.

The bottom surface 404 of the endplate trial 400 is illustrated in FIG. 4C. Bottom surface 404 may include a curved cutout 434. The curved cutout 434 may include an opening 436, a linear passageway 438, and a rounded terminus 440. The rounded terminus 440 may be coaxial with the rounded cavity 420. The curved cutout 434 may be configured to accommodate a portion of the vertebral implant device (e.g., cylindrical body 364, illustrated in FIG. 4D) therein.

Endplate trial 400 may include one or more stabilizing members. As illustrated in FIGS. 4C-D, the stabilizing members may include first and second projections 442, 444 extending from the bottom surface 404. The projections 442, 444 may have a five-sided shape (e.g., pentagonal). The projections 442, 444 may be spaced apart by a distance that can vary depending on the dimensions of the vertebral implant device with which the endplate trial 400 may be engaged. As described herein, and as illustrated in FIG. 4D, expandable trial assembly 356 may include expandable tip assembly 358 that includes, among other things, a gear member 362. The first and second projections 442, 444 may be configured to engage the gear member 362 when the expandable tip assembly 358 is in the contracted configuration. Thus, in some embodiments, the projections 442, 444 may be spaced apart by a distance that is less than a diameter of the gear member 362, as illustrated in FIG. 4D. However, in order to allow the cylindrical body 364 to pass freely along the cutout 434, the projections 442, 444 may also be spaced apart by a distance that is greater than a diameter of the cylindrical body 364.

Those skilled in the art may appreciate that the endplate trials described herein may include other coupling mechanisms or elements for reversibly coupling with a vertebral implant device having various properties. Examples of alternative coupling elements are illustrated in FIGS. 5-10. Those skilled in the art may appreciate that the features of the endplate trials illustrated in FIGS. 5-10 may be combined with each other as well as with one or more features of endplate trials 300 and 400 described herein.

Figure 5:
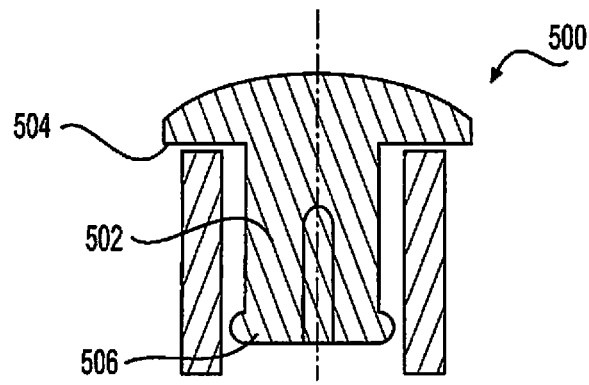
FIGS. 5, 6, 7, 8, 9, and 10 illustrate alternative embodiments of endplate trials as described herein.
Figure 6:
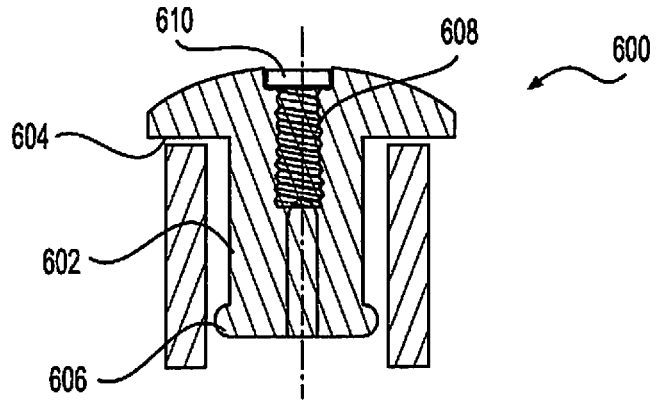

In some embodiments, the vertebral implant device may include a hollow receptacle (e.g., a hollow cylinder), and the endplate trial may include a coupling element that is configured to be received within the hollow receptacle. As illustrated in FIGS. 5-6, the endplate trial 500, 600 may include a plurality of deflectable arms 502, 602 extending from a bottom surface 504, 604 thereof. Each arm 502, 602 may include a protrusion 506, 606 that may be configured to engage or press against an inner surface of the hollow receptacle. In some embodiments, the hollow receptacle may further include a groove or depression configured to receive the protrusion 506, 606. The arm(s) 502 of endplate trial 500 may be configured to engage the hollow receptacle in a snap fit. For example, the arm(s) 502 may be squeezed into the hollow receptacle, and released once the protrusion(s) 506 are positioned at the groove. As illustrated in FIG. 6, the endplate trial 600 may further include a threaded passageway 608 and a fastener or screw member 610. In use, the screw member 610 may be advanced through the threaded passageway 608 to push or splay the arms 602 apart, thereby engaging the protrusion 606 with the inner surface of the hollow receptacle.

Figure 7:
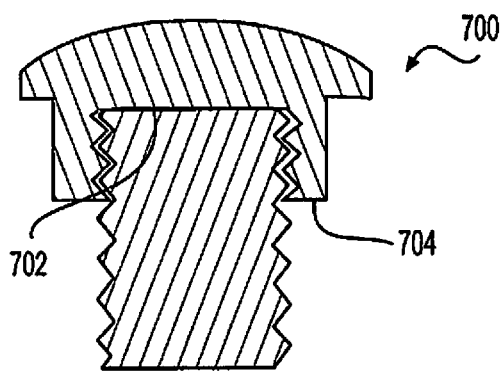
Figure 8:
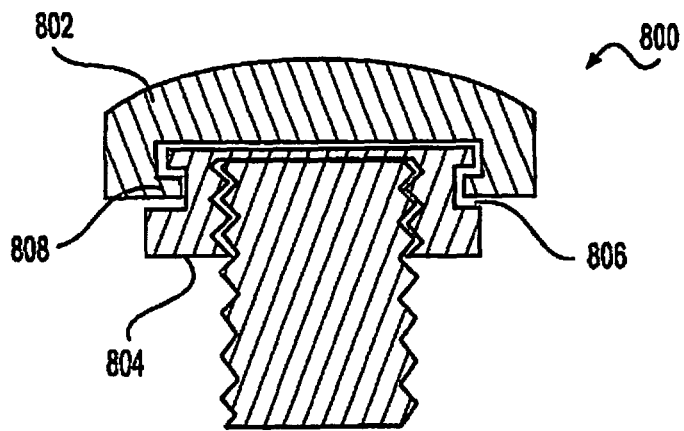

In other embodiments, the vertebral implant device may include a threaded extension member. Accordingly, FIG. 7 illustrates endplate trial 700 which includes an internally-threaded cavity 702 that may extend through a bottom surface 704 thereof. The internally-threaded cavity 702 may be configured to threadably engage (e.g., thread onto) the vertebral implant device. FIG. 8 illustrates another embodiment, endplate trial assembly 800, which includes an endplate trial 802 and a collar 804. The collar 804 can include an internally-threaded cavity and can be configured to threadably engage (e.g., thread onto) the vertebral implant device, as well as being configured to engage the endplate trial 802. The collar 804 may also include a groove or undercut 806 configured to receive a portion of the endplate trial 802, such as a lip 808. The endplate 802 may be configured to slide or snap onto the collar 804. This type of endplate trial design may be advantageous when endplate trial 802 is non-circular, as the endplate trial 802 may not be threaded directly onto the vertebral implant device.

Figure 9:
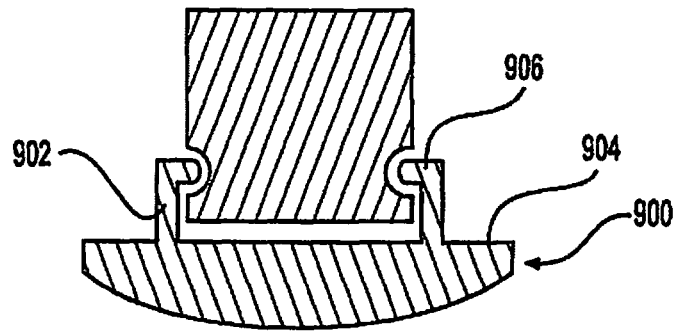
Figure 10:
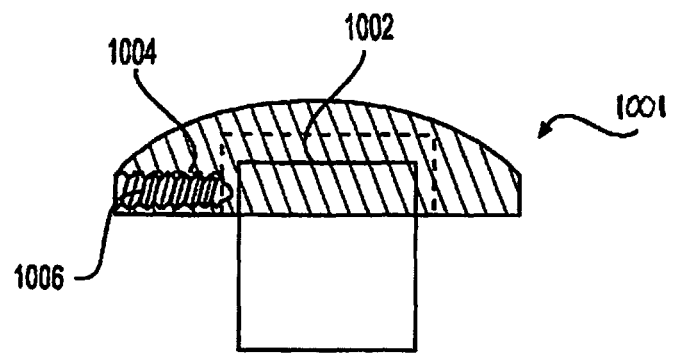

In some embodiments, the vertebral implant device may include a solid extension member, as illustrated in FIGS. 9-10. As illustrated in FIG. 9, the solid extension member may further include an undercut. In these embodiments, endplate trial 900 may include one or more arms 902 extending from a bottom surface 904. Each arm 902 may further include a protrusion 906. The arms 902 may be configured to engage an outer surface of the solid extension member, for example, in a snap fit. In use, the endplate trial 900 may be snapped or pushed onto the vertebral implant device. The arms 902 may temporarily splay or spring outwards, and upon return to a neutral position, the protrusion 906 may be retained within the undercut of the solid extension member.

FIG. 10 illustrates endplate trial 1000 which can include a coupling element which includes a cavity 1002. The cavity 1002 can be configured to receive at least a portion of the vertebral implant device therein. Endplate trial 1000 can further include a retaining element that includes a passageway 1004 that extends from a side surface to the cavity and that is configured to receive a fastener 1006 therein. The fastener 1006 may include, for example, a ball plunger, a spring plunger, or a screw. In use, the endplate trial 1000 may be configured like a set screw collar, wherein the fastener 1006 may be threaded into the passageway 1004 until it contacts and engages the vertebral implant device in a friction fit.

Embodiments herein are also directed to methods of inserting a vertebral implant. In some embodiments, the method can include providing a vertebral trial, such as expandable trial assembly 356, and at least one endplate trial as described herein, such as endplate trial 300 or endplate trial 400. The expandable trial assembly 356 may be provided, for example, in a partially contracted configuration. The method can further include coupling the endplate trial with the vertebral trial, for example, by sliding a portion of the vertebral trial (e.g., disc 360) laterally into an undercut on the endplate trial and retaining the disc 360 within a rounded cavity thereof. The method can further include positioning the overall assembly (e.g., expandable trial assembly coupled to at least one trial endplate) between two vertebrae, for example, as part of a corpectomy procedure. The expandable tip assembly 358 of the expandable trial assembly 356 may then be expanded, for example, by causing the gear member 362 to rotate. The expandable tip assembly 358 may be expanded until the top surface of the endplate trial contacts a vertebral body and/or the desired spinal alignment is attained. The method can further include measuring expansion of the overall assembly, for example, with a scale at a proximal end of the expandable trial assembly 356. As described herein, the endplate trials can advantageously enable or promote measurement of footprint, angulation, and height in one step or procedure. Once measurements are taken, the overall assembly may be removed from the vertebral space. This step may then include contracting or retracting the overall assembly. As described herein, when in a contracted configuration, the protrusions on the bottom surface of the endplate trial may engage a portion of the expandable tip assembly (e.g., gear member 362), thereby providing enhanced stability and reducing the likelihood that the endplate trial unintentionally uncouples from the expandable trial assembly 356 during the removal step. Those skilled in the art may appreciate that if one or more parameters of the particular endplate trial is unacceptable, the endplate trial may be uncoupled or removed from the expandable trial assembly 356 and exchanged for a different endplate trial. Thus, the readily interchangeable nature of the endplate trials described herein may enable a surgeon to easily try out various endplate trials and quickly obtain the appropriate measurements. Once the proper measurements are obtained, an implant (e.g., an expandable implant, optionally including one or more polyaxial endplate assemblies described herein) may be selected on the basis of these measurements. Thereafter, the method can further include positioning the selected implant between the vertebrae and expanding the implant based on the measured expansion of the expandable trial assembly 356.

Figure 11A:
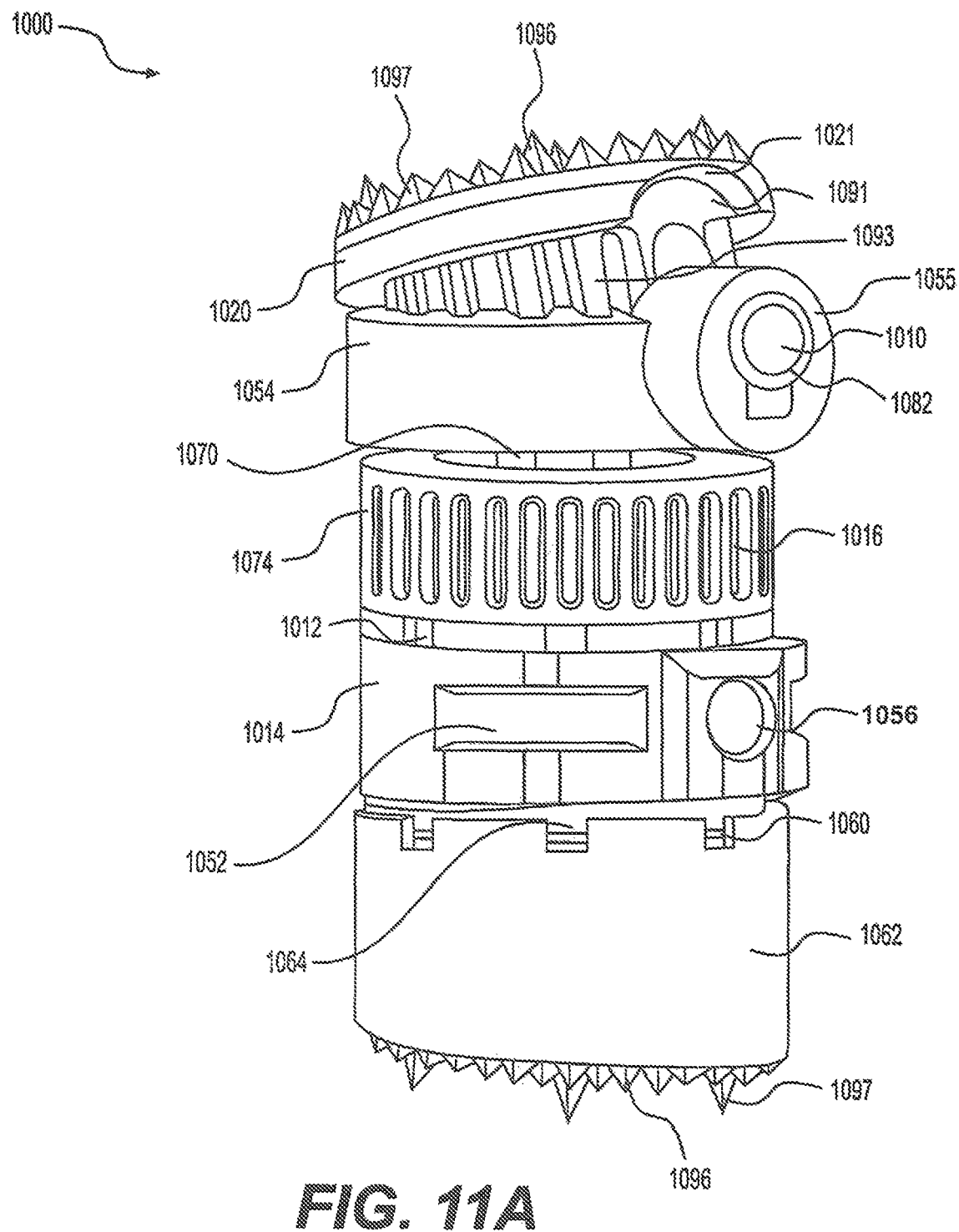
FIG. 11A illustrates a view of an alternative expandable vertebral implant in accordance with some embodiments.

FIG. 11A illustrates a view of an alternative expandable vertebral implant in accordance with some embodiments. In some embodiments, the expandable vertebral implant 1000 can comprise an interbody spacer, such as a corpectomy device including a polyaxial endplate assembly. The polyaxial endplate assembly, which includes an endplate 1020 capable of polyaxial adjustability, a receptacle for receiving the endplate 1020 therein, and a securing element 1010 for locking the angular position of the endplate 1020, advantageously accommodates natural kyphosis or lordosis of a patient. As opposed to different interbody spacers, which do not have angulating or polyaxial endplates and thus require a surgeon to guess on the type of endplate that should conform to a patient's endplate, the polyaxial endplate assembly provided herein eliminates the guesswork and eases the insertion of the implant 1000 into the patient.

The expandable vertebral implant 1000 comprises an interbody spacer such as a corpectomy device capable of expanding across one or more vertebral levels. The expandable vertebral implant 1000 comprises an upper endplate 1020 and a lower endplate 1062 that are capable of expanding away from one another to engage respective upper and lower vertebral endplates. In the present embodiment, the lower endplate 1062 is non-polyaxial, while the upper endplate 1020 is part of a polyaxial endplate assembly and capable of different angulations. In other embodiments, the lower endplate 1062 can be part of a polyaxial endplate assembly while the upper endplate 1020 can be non-polyaxial. In yet other embodiments, both the upper endplate 1020 and the lower endplate 1062 can be part of polyaxial endplate assemblies. These endplates 1020, 1062 will be discussed further below.

To expand the distance of separation between the upper endplate 1020 and the lower endplate 1062, the implant 1000 includes an inner member 1012, an outer member 1014 and a gear member 1016. Each of these components is akin to the similarly named components in FIG. 2 of U.S. 2011/0251691 to McLaughlin (incorporated by reference in its entirety), and operate in a similar manner. The upper endplate 1020 is attached to the inner member 1012 via coupling elements 1070 (shown in FIGS. 11A and 14A-14D), while the lower endplate 1062 is attached to the outer member 1014 via similar coupling elements 1060. In particular, as the gear member 1016 is rotated, this causes the inner member 1012 to thread and rotate upwardly, thereby causing the upper endplate 1020 to expand away from the lower endplate 1062. The upper endplate 1020 can expand until it firmly contacts an upper vertebral endplate of a patient. Upon contact with the upper vertebral endplate, the upper endplate 1020 can adjust polyaxially to match the natural anatomy of the patient until it is securely locked in a desired angulated position.

The outer member 1014 comprises one or more mounting features or slots 1052, and a threaded opening 1054. The slots 1052 and the threaded opening 1054 are capable of being engaged by an expansion tool including a gear attached thereon (shown for example in FIG. 8 of incorporate U.S. 2011/0251691). The tool gear is capable of engaging the gear member 1016 via its gear teeth 1074, thereby causing rotation of the gear member 1016. In some embodiments, the outer member 1014 is formed of a polymer, such as PEEK.

The inner member 1012 comprises outer threads that extend along its longitudinal axis. As the gear member 1016 is rotated by the expansion tool, inner threads of the gear member 1016 engage the outer threads of the inner member 1012, thereby causing the inner member 1012 to thread and move upwardly. In some embodiments, the inner member 1012 is formed of a polymer, such as PEEK.

The outer member 1014 is attached to a bottom endplate 1062. In the present embodiment, the bottom endplate 1062 is non-polyaxial and has a fixed angle. In other embodiments, the bottom endplate 1062 can be part of a polyaxial assembly. The bottom endplate 1062 comprises one or more protrusions, engagement members, teeth or spikes 1096 for initially engaging a lower vertebral endplate. In addition, the bottom endplate 1062 comprises one or more protrusions, engagement members, teeth or spikes 1097 that are shorter, but higher in number, than the spikes 1096. In addition, the bottom endplate 1062 includes one or more relief spaces or slots 1064 that are configured to engage and connect with tabs 1060 of the outer member 1014, thereby connecting the two components together. In some embodiments, the bottom endplate 1062 is formed of a metal or metal alloy, such as titanium.

The inner member 1012 is attached to a polyaxial endplate assembly. In the present embodiment, the polyaxial endplate assembly comprises an upper endplate 1020, a receptacle 1054 for receiving the upper endplate 1020, and a securing element 1010. The upper endplate 1020 comprises an upper portion and a lower portion. The upper portion of the upper endplate 1020 comprises one or more protrusions, engagement members, teeth or spikes 1096 for initially engaging an upper vertebral endplate. In addition, the upper endplate 1020 comprises one or more protrusions, engagement members, teeth or spikes 1097 that are shorter, but higher in number, than the spikes 1096. The lower portion of the upper endplate 1020 comprises a downwardly extending extension portion 1091 having geared or splined features 1093. The splined features 1093 advantageously provide torsional stability to the upper endplate 1020, which is received in the receptacle 1054. In addition, the upper endplate 1020 includes an arched clearance region 1021, which accommodates and provides clearance for the flanged portion 1055 of the receptacle 1054, discussed further below. In some embodiments, the upper endplate 1020 is formed of a metal or metal alloy, such as titanium.

Figure 13:
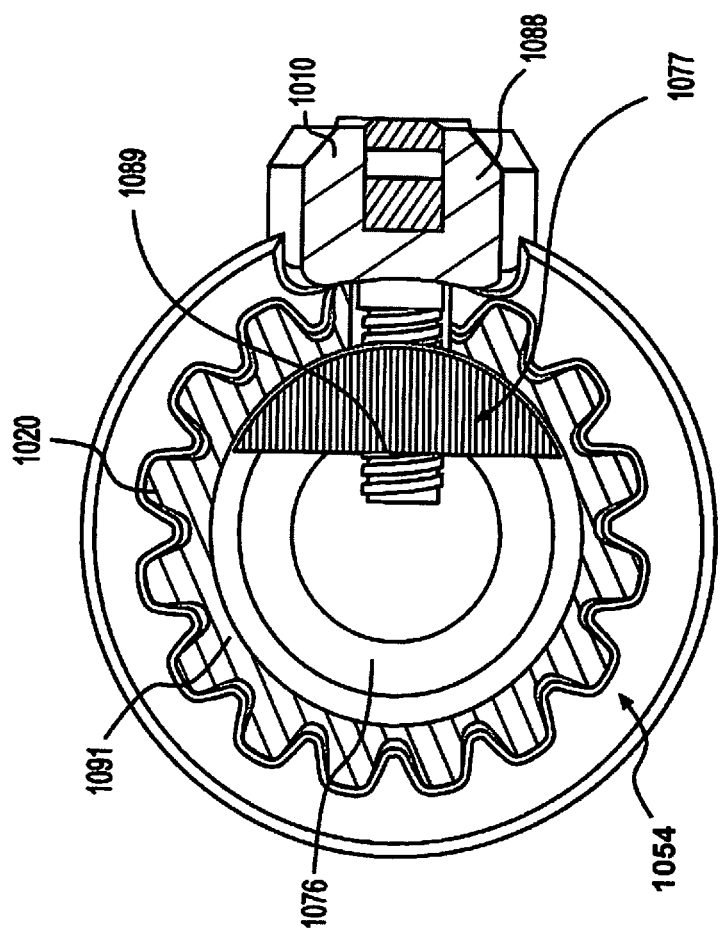
FIG. 13 shows a top cross-sectional view of the polyaxial endplate assembly of FIG. 12.

The receptacle 1054 (shown best in FIG. 11B) comprises an upper portion and a lower portion. The upper portion of the receptacle 1054 comprises an annular body attached to a flanged portion 1055. The flanged portion 1055 includes a tool receiving recess 1082 formed therethrough, which is configured to receive a securing element 1010 therein. The securing element 1010 (also shown in FIG. 11B) comprises a head portion 1088 and a threaded shaft portion 1089. The threaded shaft portion 1089 is designed to engage with clamping nut 1077 (also shown in FIG. 11B) to form a locking system that secures the upper endplate 1020 in a desired angular position or orientation. As the securing element 1010 is threaded into the clamping nut 1077, a clamp is formed between the two members with the upper endplate 1020 compressed therebetween (as shown in FIG. 13), thereby securing the upper endplate 1020 in the desired angular position or orientation. The lower portion of the receptacle 1054 comprises a stem or neck portion 1076 configured to extend through the inner member 1012. In addition, the receptacle 1054 further comprises coupling elements 1070 in the form of tabs designed to interdigitate with tabs 1038 of the inner member 1012, thereby securing the receptacle to the inner member 1012.

In some embodiments, the expandable vertebral implant 1000 operates as follows. After one or more intervertebral discs and optionally, one or more vertebrae, are removed, the implant 1000 can be inserted into the cavity. Spikes 1096 on the lower endplate 1062 of the implant 1000 can engage a lower vertebral endplate. With the implant 1000 in the cavity, an expansion tool having a gear can engage and rotate the gear member 1016, which causes the inner member 1012 to expand upwardly away from the outer member 1014 of the implant 1000, thereby causing the upper endplate 1020 to separate away from the lower endplate 1062. As the upper endplate 1020 expands upwardly, it contacts an upper vertebral endplate. The upper endplate 1020 is capable of polyaxial movement and will advantageously conform to the natural anatomy of the spine, including any kyphosis or lordosis in the patient. Once the upper endplate 1020 has conformed to the natural anatomy, the securing element 1010 can be actuated and rotated, thereby locking the upper endplate 1020 in a desired angular position. The expandable vertebral implant 1000 can thus serve as a corpectomy device that promotes fusion across one or more levels of the spine.

Figure 11B:
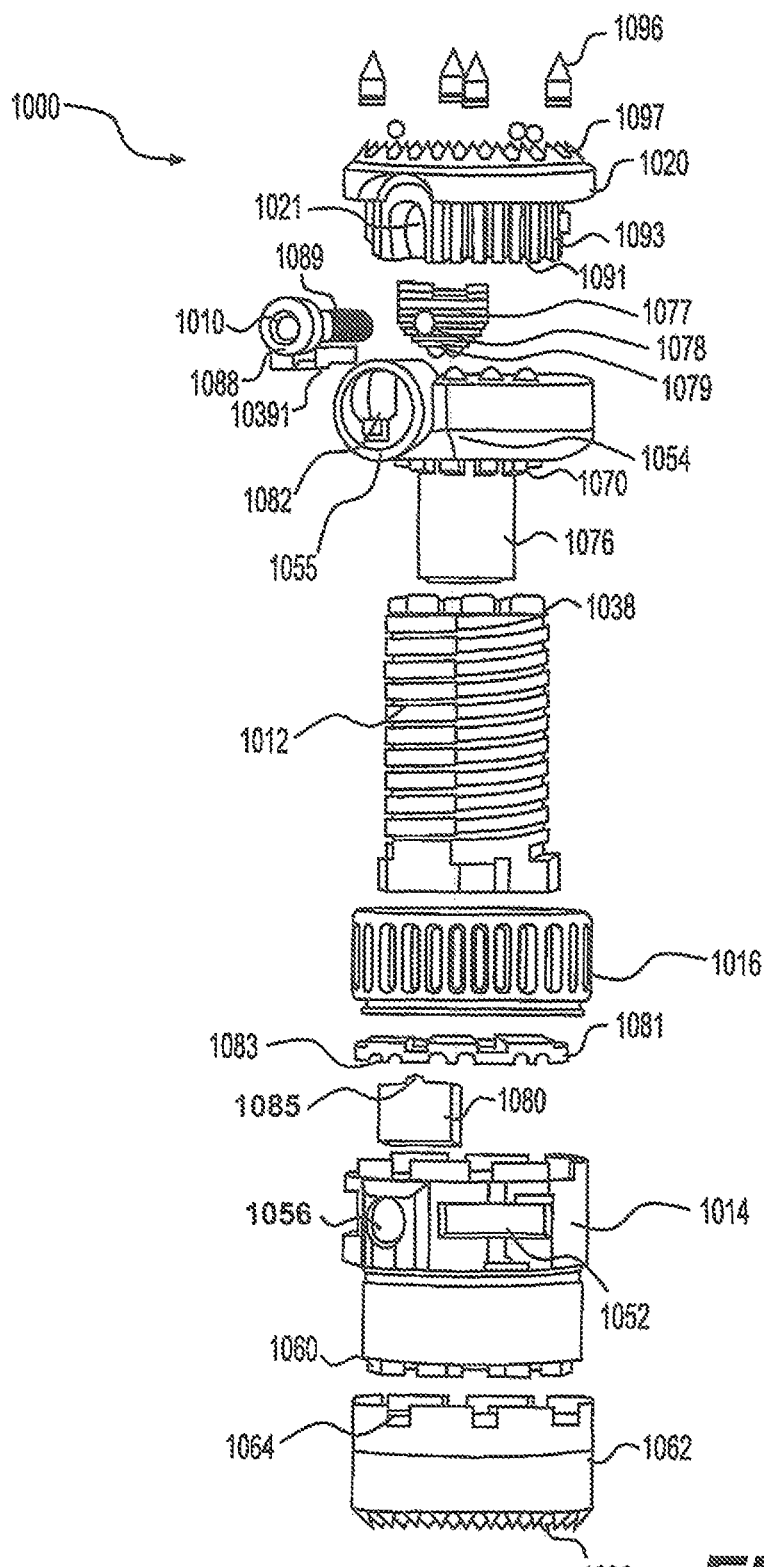
FIG. 11B illustrates an exploded view of the alternative expandable vertebral implant of FIG. 11A.

FIG. 11B illustrates an exploded view of the alternative expandable vertebral implant of FIG. 11A. The exploded view shows components discussed above including the inner member 1012, the outer member 1014, the gear member 1016, the upper endplate 1020, and the lower endplate 1062. Additional features, including the locking system comprising the securing element 1010 and the clamping nut 1077, as well as the lock ring 1081 and locking member 1080, which were not as easily visible in FIG. 11A, are clearly shown. These additional features are discussed below.

The exploded view in FIG. 11B shows the various components of the locking system that will secure the upper endplate 1020 in a desired angular position. The locking system comprises a securing element 1010, a clamping nut 1077 and a stabilization pin 1093. As discussed previously, the securing element 1010 includes a head portion 1088 and a shaft portion 1089 that extends through the recess 1082 in the receptacle 1054. As shown in FIG. 11B, the securing element 1010 then extends into an opening 1078 formed through the clamping nut 1077. Portions of the upper endplate 1020 are positioned between the securing element 1010 and the clamping nut 1077, such that rotation of the securing element 1010 draws in the clamping nut 1077, causing the members to clamp and secure the upper endplate 1020 in a desired angular position.

The clamping nut 1077 includes an opening 1078 for receiving the securing element 1010 therethrough. In addition, below the opening 1078 is a lower recess 1079 for receiving a stabilizing pin 1093, which is discussed in more detail below. As shown in FIG. 11B, the clamping nut 1077 comprises a ridged outer surface. The advantage of the ridged outer surface is that as the clamping nut 1077 abuts the upper endplate 1020 (which could be formed of PEEK), the ridges bite and dig into endplate 1020, thereby creating a better engagement between the two components.

Figure 12:
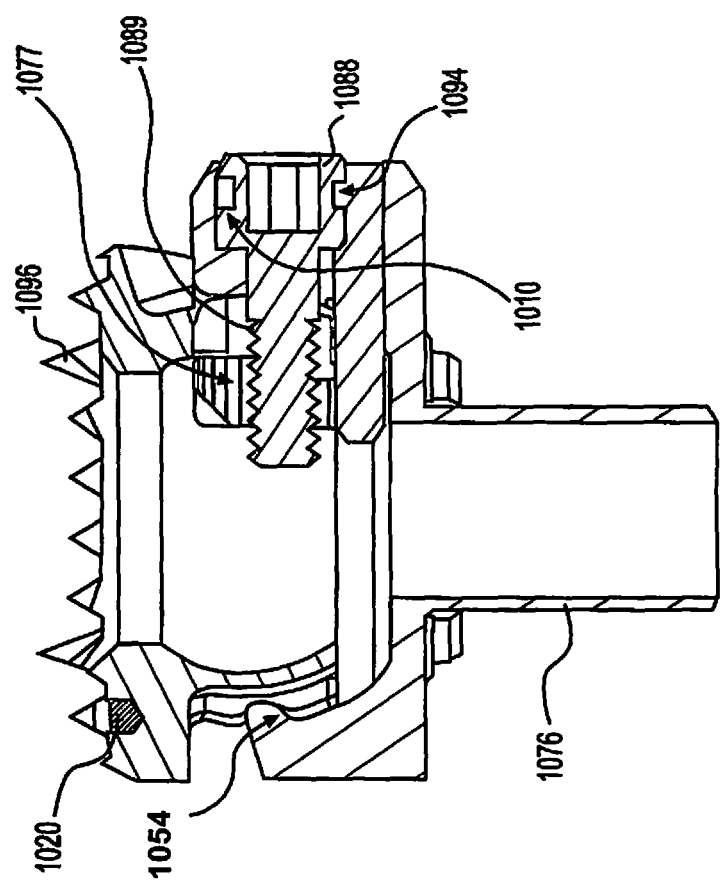
FIG. 12 illustrates a side cross-sectional view of a polyaxial endplate assembly of the implant of FIGS. 11A and 11B.

In addition to the securing element 1010 and the clamping nut 1077, the locking system comprises a stabilization pin 1093. In some embodiments, the stabilization pin 1093 comprises a Woodruff key. The stabilization pin 1093 is configured to extend through the recess 1082 and into the lower recess 1079 of the clamping nut 1077. The stabilization pin 1093 advantageously serves as a counter or anti-torque to prevent the clamping nut 1077 from rotating. As shown in FIG. 12, the stabilization pin 1093 can comprise a cut-out portion 1094 that is designed to engage the head portion 1088 of the securing element 1010, which advantageously helps to steady the stabilization pin 1093 during use.

In addition to the locking system that secures the angulation of the upper endplate 1020, the implant 1000 comprises a separate locking system that restricts relative movement between the inner member 1012 and the outer member 1014. This locking system comprises a locking member 1080 and a lock ring 1081. The lock ring 1081 is designed to interdigitate with and engage the gear member 1016. The locking member 1080 comprises a protrusion, nub or tab 1082 that is designed to fit within a recess 1083 of the lock ring 1081. When an expansion tool is not operating the implant 1000, the protrusion 1082 of the locking member 1080 resides in the recess 1083 of the lock ring 1081, thereby restricting movement between the inner member 1012 and outer member 1014. When an expansion tool is inserted into the implant 1000, it pushes in the locking member 1080 such that the protrusion 1082 is pushed out of the recess 1083, thereby allowing relative movement between the inner member 1012 and outer member 1014.

FIG. 12 illustrates a side cross-sectional view of a polyaxial endplate assembly of the implant of FIGS. 11A and 11B. FIG. 13 shows a top cross-sectional view of the polyaxial endplate assembly of FIG. 12. From these views, one can see how the locking system including the securing element 1010 and the ridged clamping nut 1077 are configured to secure the upper endplate 1020 therein.

The polyaxial endplate assembly of FIG. 12 can have different angulations. The upper endplate 1020 is capable of angulating relative to a horizontal plane along 360 degrees. In some embodiments, the upper endplate 1020 can angle between 0 and 45 degrees. In other embodiments, between 0 and 30 degrees. And in yet other embodiments between 0 and 15 degrees. Advantageously, the polyaxial endplate assembly conforms to the natural anatomy of a patient, thereby saving time on the part of the surgeon who would no longer have to guess at which type of implant to insert into a patient. In addition, by conforming to the natural anatomy of a patient, the polyaxial endplate assembly evenly distributes load, thereby reducing stress concentrations that would could occur in non-comforming endplates.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims. Although individual embodiments are discussed herein, the invention covers all combinations of all those embodiments.

What is claimed is:

1. An expandable vertebral implant assembly comprising:
an inner member;
an outer member;
a gear member, wherein rotation of the gear member causes relative movement between the inner member and the outer member; and
a polyaxial endplate assembly including an endplate, the endplate having a plate portion and a rounded body extending below the plate portion,
wherein the endplate of the polyaxial endplate assembly is capable of pivoting along at least two intersecting axes disposed in the same plane which is not parallel to a central longitudinal axis of the expandable vertebral implant,
wherein the polyaxial endplate assembly includes a receiving member attached to at least one of the inner member and the outer member, a locking member having a locking body disposed behind the rounded body of the endplate, a wedge member configured to be received in the receiving member, and a securing element configured to be received in the receiving member,
wherein the securing element abuts the wedge member, and
wherein the endplate is capable of pivoting with respect to the receiving member,
wherein the securing element is adapted to push the wedge member to apply pressure against the locking member such that the locking body presses the rounded body of the endplate against an internal surface of the receiving member.

2. The assembly of claim 1, wherein the polyaxial endplate assembly comprises a receptacle for receiving the securing element.

3. The polyaxial endplate assembly of claim 1, wherein the wedge member is asymmetrical along a longitudinal plane.

4. The polyaxial endplate assembly of claim 1, wherein the wedge member comprises an upper wall and a lower wall, and wherein the lower wall is steeper than the upper wall.

5. The polyaxial endplate assembly of claim 4, wherein the lower wall of the wedge member is configured to engage the locking member and the upper wall of the wedge member is configured to engage the receiving member.

6. The polyaxial endplate assembly of claim 1, wherein the securing element comprises an end that is configured to contact the wedge member.

7. The polyaxial endplate assembly of claim 1, wherein the securing element comprises a set screw.

8. An expandable vertebral implant assembly comprising:
an inner member;
an outer member;
a gear member, wherein rotation of the gear member causes relative movement between the inner member and the outer member;
a polyaxial endplate assembly including an endplate, the endplate having a plate portion and a rounded body extending below the plate portion; and
a fixed endplate assembly attached to the other of the inner member and the outer member
wherein endplate of the the polyaxial endplate assembly is capable of pivoting along at least two intersecting axes disposed in the same plane which is not parallel to a central longitudinal axis of the expandable vertebral implant, wherein the polyaxial endplate assembly includes a receiving member attached to at least one of the inner member and the outer member, a locking member having a locking body disposed behind the rounded body of the endplate, a wedge member configured to be received in the receiving member, and a securing element configured to be received in the receiving member, wherein the securing element abuts the wedge member, and wherein the endplate is capable of pivoting with respect to the receiving member, wherein the securing element is adapted to push the wedge member to apply pressure against the locking member such that the locking body presses the rounded body of the endplate against an internal surface of the receiving member.

9. The assembly of claim 8, wherein the inner member includes outer threads that are capable of engagement with inner threads of the gear member.

10. The assembly of claim 8, wherein the polyaxial endplate assembly comprises a receptacle for receiving the securing element.

11. The polyaxial endplate assembly of claim 8, wherein the wedge member is asymmetrical along a longitudinal plane.

12. The polyaxial endplate assembly of claim 8, wherein the wedge member comprises an upper wall and a lower wall, and wherein the lower wall is steeper than the upper wall.

13. The polyaxial endplate assembly of claim 12, wherein the lower wall of the wedge member is configured to engage the locking member and the upper wall of the wedge member is configured to engage the receiving member.

14. The polyaxial endplate assembly of claim 8, wherein the securing element comprises an end that is configured to contact the wedge member.

15. The polyaxial endplate assembly of claim 8, wherein the securing element comprises a set screw.

* * * * *